US008423294B2

(12) United States Patent
Nadel et al.

(10) Patent No.: US 8,423,294 B2
(45) Date of Patent: Apr. 16, 2013

(54) HIGH RESOLUTION LINEAR ANALYSIS OF POLYMERS

(75) Inventors: Mark Nadel, Westborough, MA (US);
Eugene Y. Chan, Brookline, MA (US);
Martin Fuchs, Uxbridge, MA (US);
Rudolf Gilmanshin, Waltham, MA (US)

(73) Assignee: PathoGenetix, Inc., Woburn, MA (US)

( * ) Notice: Subject to any disclaimer, the term of this patent is extended or adjusted under 35 U.S.C. 154(b) by 1646 days.

(21) Appl. No.: 10/762,207

(22) Filed: Jan. 21, 2004

(65) Prior Publication Data

US 2004/0235014 A1 Nov. 25, 2004

Related U.S. Application Data

(63) Continuation-in-part of application No. 10/246,779, filed on Sep. 18, 2002, now abandoned.

(60) Provisional application No. 60/322,981, filed on Sep. 18, 2001.

(51) Int. Cl.
*G01N 33/50* (2006.01)

(52) U.S. Cl.
USPC .......................................................... 702/19

(58) Field of Classification Search ........................ None
See application file for complete search history.

(56) References Cited

U.S. PATENT DOCUMENTS

| 5,200,313 | A | 4/1993 | Carrico |
| 5,422,271 | A | 6/1995 | Chen et al. |
| 5,858,671 | A | 1/1999 | Jones |
| 5,912,127 | A | 6/1999 | Narod et al. |
| 6,020,126 | A | 2/2000 | Carlsson et al. |
| 6,150,089 | A | 11/2000 | Schwartz |
| 6,210,896 | B1 | 4/2001 | Chan |
| 6,225,067 | B1 | 5/2001 | Rogers |
| 6,246,046 | B1 | 6/2001 | Landers et al. |
| 6,248,537 | B1 | 6/2001 | Bensimon et al. |
| 6,263,286 | B1 * | 7/2001 | Gilmanshin et al. ............ 702/19 |
| 6,294,136 | B1 | 9/2001 | Schwartz |
| 6,355,420 | B1 * | 3/2002 | Chan ................................ 435/6 |
| 6,403,311 | B1 | 6/2002 | Chan |
| 6,696,022 | B1 | 2/2004 | Chan et al. |

FOREIGN PATENT DOCUMENTS

| WO | WO 98/35012 A3 | 8/1998 |
| WO | WO 98/49344 A1 | 11/1998 |
| WO | WO 00/09757 A1 | 2/2000 |
| WO | WO 01/13088 A1 | 2/2001 |

OTHER PUBLICATIONS

Bezrukov et al., "Counting Polymers Moving Through a Single Ion Channel", Nature, 370: 279-281, 1994.
Bustamante, "Direct Observation and manipulation of Single DNA Molecules Using Fluorescence Microscopy", Annu. Rev. Biophys. Biophys. Chem., 20:415-446, 1991.
Gurrieri et al., "Imaging of Kinked Configurations of DNA Molecules Undergoing Orthogonal Field Alternating Gel Electrophoresis by Fluorescence Microscopy", Biochem., 29:3396-3401, 1990.
Kasianowicz et al., "Characterization of Individual Polynucleotide Molecules Using a membrane Channel" Proc. natl. Acad. Sci. USA, 93:13770-13773, 1996.
Matsumoto et al., "Light Microscopic Structure of DNA in Solution Studied by the 4',6-Diamidino-2-phenylindole Staining Method", Dept of Biophys, Faculty of Science, Kyoto University, Kyoto 606, Japan, pp. 501-516, 1981.
Meng et al., "Optical Mapping of Lambda Bacteriophage Clones Using Restriction Endonucleases", Nat. Genetics, 9:432-438, 1995.
Wittwer et al., Continuous Fluorescence Monitoring of Rapid Cycle DNA Amplification. BioTechniques, Jan. 1997, vol. 22, No. 1, pp. 130-138.
Thomann et al., Automatic fluorescent tag detection in 3D with super-resolution: application to the analysis of chromosome movement. J Microsc. Oct. 2002;208(Pt 1):49-64.

* cited by examiner

*Primary Examiner* — Jason Sims

(74) *Attorney, Agent, or Firm* — Wolf, Greenfield & Sacks, P.C.

(57) ABSTRACT

The invention provides methods and systems for improved spatial resolution of signal detection, particularly as applied to the analysis of polymers such as biological polymers. Some of the methods and systems comprise differentially tagging polymers in order to increase resolution. Some of the methods and systems comprise techniques for improving the precision of separation distance measurements, without necessarily requiring improvements in the known detection resolution of prior art systems.

35 Claims, 8 Drawing Sheets

HIGH RESOLUTION LINEAR ANALYSIS OF POLYMERS

CROSS REFERENCE TO RELATED APPLICATIONS

This application also claims the benefit of and is a continuation-in-part of U.S. patent application Ser. No. 10/246,779 filed on Sep. 18, 2002, now abandoned which claims the benefit of U.S. Provisional Patent Application No. 60/322,981 filed on Sep. 18, 2001.

FIELD OF THE INVENTION

The invention relates to linear analysis of sequence information for polymers such as biological polymers, and provides improved spatial resolution of signal detection systems.

BACKGROUND OF THE INVENTION

Sequence analysis of polymers has many practical applications. Of great interest is the ability to sequence the genomes of various organisms, including the human genome. Specific sequences can be recognized with a host of sequence-specific tagging methods such as various types of probes, engineered proteins, and also synthetic compounds. In any of these sequence-specific tagging approaches, there is always a need to resolve adjacent tags, in order to achieve higher resolution and thus map as much of the polymer as possible.

Linear analysis of DNA can be accomplished by analysis of fixed DNA molecules, analysis of moving DNA molecules, and analysis of DNA molecules using readers such as molecular motors or proteins capable of scanning along the length of a DNA strand. These approaches make use of a number of signals and detection systems to acquire the information from the sequence-specific tags on the polymer. For instance, fluorescence, atomic force microscopy (AFM), scanning tunneling microscopy (STM), as well as other electrical and electromagnetic methods, are suitable for capturing signals and thereby "reading" the sequence information of a polymer. All of these methods can be characterized and limited by their spatial resolution. Spatial resolution defines the minimum distance two adjacent probe molecules (e.g., sequence-specific tags) can be separated from each other and still be simultaneously detected as distinct, separate signals.

Fluorescence detection is often carried out by imaging. Optical resolution of fluorescence detection systems defines the smallest distance between probes at which they can still be distinguished. This distance is determined by diffraction. In a confocal microscopy system, in which the sample is illuminated and viewed through a pinhole in the image plane, the pinhole size determines the lateral resolution under uniform illumination of the pinhole. A confocal microscope system can be used in combination with a flow system that moves a target molecule (e.g., DNA or RNA) through a detection spot in the focal plane of the microscope. If the target molecules are stretched out in the direction of motion, and moved singly through the detection spot, then bound fluorescently labeled probes can be sequentially detected as they enter the detection spot. If the velocity of the target polymer is known, then the distance between detected probes can be determined from the time between sequential signals. According to prior art systems, probes that are spatially separated by more than the spot size can be distinguished from each other.

There is a need for increasing the resolution of detection systems in order to increase the amount of data captured from polymer analysis approaches.

SUMMARY OF THE INVENTION

The invention is based, in part, on the discovery that differential tagging of sequence specific probes allows the positions of such probes to be determined with greater spatial resolution than could be achieved previously. The invention increases the efficiency of polymer sequence analysis by increasing the amount of data that can be captured per a single analysis. Current methods of polymer analysis are limited by the spatial resolution of the detection system used. The invention increases the spatial resolution of several detection systems, thereby allowing for a greater amount of sequence information to be obtained during individual runs. Aspects of the invention provide both methods and systems for analyzing polymers based on these discoveries.

The invention is also based, in part, on improving the precision with which separation distances are measured, regardless of whether the separation distance is within the spatial resolutions of prior art systems.

In one aspect, the invention provides a method for analyzing a polymer that comprises providing the polymer bound to first and second unit specific markers. The first unit specific marker includes a first label and the second unit specific marker includes a second label, wherein the first and second unit specific markers are spaced apart on the polymer by a separation distance. The method includes providing a detection zone adapted to detect emission signals, the detection zone characterized by a zone distance; establishing a timing event; moving the polymer through the detection zone at a velocity; detecting a first emission signal emitted by the label of the first unit specific marker as the first unit specific marker passes through the detection zone; detecting a second emission signal emitted by the label of the second unit specific marker as the second unit specific marker passes through the detection zone; calculating a proportion of the first emission signal and a proportion of the second emission signal, that are each detected on a side of the timing event; and determining the separation distance by comparing the proportion of the first signal and the proportion of the second signal to determine the separation distance in analyzing the polymer.

Some embodiments of the invention include a computer-readable medium having computer-readable signals stored thereon that define instructions that, as a result of being executed by a computer, instruct the computer to perform a method of determining a separation distance between a first and a second label on a polymer in a system having a detection zone characterized by a zone distance and adapted to detect a first emission signal and a second emission signal from the first and second label, respectively, when they pass through the detection zone at a velocity. The method comprises acts of establishing a timing event; calculating a proportion of the first emission signal and calculating a proportion of the second emission signal that are each detected before the timing event; and determining the separation distance by comparing the proportion of the first signal and the proportion of the second signal to determine the separation distance.

In one embodiment, calculating the proportion of the first emission signal comprises dividing a first portion of the first signal that is detected before the timing event by all of the first signal.

In some embodiments, calculating the proportion of the second emission signal comprises dividing a first portion of the second signal that is detected before the timing event by all of the second signal In some embodiments, calculating the proportion of the first emission signal comprises dividing a second portion of the first signal that is detected after the timing event by all of the first signal.

In some embodiments, calculating the proportion of the second emission signal comprises dividing a second portion of the second signal that is detected after the timing event by all of the second signal.

In some of the embodiments, the timing event comprises a single timing event for calculating the proportion of the first emission signal and the proportion of the second emission signal. Furthermore, in some of these embodiments, determining the separation distance comprises multiplying the proportion of the first signal and the proportion of the second signal by the zone distance to define a first distance and a second distance, respectively; and then subtracting the second distance from the first distance to define the separation distance. Still, in some of these embodiments, determining the separation distance comprises subtracting the proportion of the second signal from the proportion of the first signal to define a separation factor; and then multiplying the separation factor by the zone distance to define the separation distance.

In further embodiments, the timing event comprises two distinct timing events, a first timing event for calculating the proportion of the first emission signal and a second timing event that occurs one reset time immediately after the first timing event, the second timing event for calculating the proportion of the second emission signal.

Some of the embodiments further comprise calculating a reset distance by multiplying the velocity by the reset time; wherein determining the separation distance comprises multiplying the proportion of the first signal and the proportion of the second signal by the zone distance to define a first distance and a second distance, respectively; then subtracting the second distance from the first distance; and then adding the reset distance to the first distance to define the separation distance.

However, other embodiments further comprise, calculating a reset distance by multiplying the velocity by the reset time; wherein determining the separation distance comprises subtracting the proportion of the second signal from the proportion of the first signal to define a separation factor; then multiplying the separation factor by the zone distance; and then adding the reset distance to define the separation distance.

In one embodiment, the timing event comprises two distinct timing events, a first timing event for calculating the proportion of the first emission signal and a second timing event that occurs later and is separated one or more timing events within a series of timing events, the second timing event for calculating the proportion of the second emission signal.

Some of the embodiments further comprise calculating a reset distance by multiplying the velocity by the reset time; wherein determining the separation distance comprises multiplying the proportion of the first signal and the proportion of the second signal by the zone distance to define a first distance and a second distance, respectively; and further wherein the second distance is subtracted from the first distance and a number of reset distances equivalent to the number of timing events, are added to the first distance to define the separation distance. Some of these embodiments further comprise calculating a reset distance by multiplying the velocity by the reset time; wherein determining the separation distance comprises subtracting the proportion of the second signal from the proportion of the first signal; and further wherein the separation factor is multiplied by the zone distance and a number of reset distances, equivalent to the number of timing events, are added to define the separation distance.

In some embodiments, the first label and the second label are distinct types of labels.

In some embodiments, the first label and the second label comprise similar types of labels.

In some embodiments, the first unit specific marker is different from the second unit specific marker. Still, in some embodiments, the first unit specific marker is identical to the second unit specific marker. Also, in some embodiments the polymer is labeled with a third unit specific marker comprising a third label.

In some embodiments, the reset time is between 0.01 and 1000 milliseconds.

In further embodiments, the detection zone is circular and the detection distance is a diameter of the detection zone.

In one embodiment, the invention provides a method for analyzing a polymer comprising (a) providing a detection station having a known detection resolution; (b) labeling the polymer with first and second unit specific markers, the first unit specific marker including a first label and the second unit specific marker including a second label distinct from the first label, wherein the first and second unit specific markers are spaced apart on the polymer such that, if the labels were not distinct from each other, they would be separated by a distance less than the known detection resolution; (c) exposing the polymer labeled as in (b) to the detection station to produce distinct first and second signals arising from the first and second labels; and (d) identifying the distinct first and second signals.

In one embodiment, the first unit specific marker is different from the second unit specific marker, either in its nature or in the polymer unit it recognizes and binds to. In another embodiment, the first unit specific marker is identical to the second unit specific marker, yet the first and second unit specific markers are labeled with distinct labels.

Unit specific markers may be referred to as being "identical to each other" if, although of different nature, they recognize and bind to the same polymer unit or sequence. The nature of a unit specific polymer refers to its composition (e.g., nucleic acid, peptide, carbohydrate, etc.) rather than its sequence specificity.

In one embodiment, the first unit specific marker and the second unit specific marker are positioned at consecutive units along the length of the polymer (i.e., immediately adjacent to one another). In another embodiment, the first unit specific marker and the second unit specific marker are spatially separated from one another by at least one unit, or at least two units.

In a further embodiment, the polymer is labeled with a third unit specific marker.

Preferably, the third unit specific marker comprises a third label. The third unit specific marker may be positioned relative to the first and second unit specific markers such that the signal produced by the third unit specific marker is above system detection resolution with respect to the signals of the first and second unit specific markers. In other words, the third unit specific marker is spaced apart from the first and second unit specific markers by a distance greater than the known detection resolution.

In some embodiments, the third unit specific marker is used as a standard from 30 which to compare multiple data sets.

The embodiments recited throughout are intended to apply equally to the various aspects of the invention.

The polymer may be a biological molecule, but is not so limited. In important embodiments, the polymer is a peptide or a nucleic acid molecule. In some preferred embodiments, the polymer is a nucleic acid molecule that is genomic DNA. In some embodiments, the unit specific markers, including the first, second and subsequent unit specific markers, are nucleic acid molecules. In other embodiments, the first, second and subsequent unit specific markers are peptide nucleic acid (PNA) molecules (such as bisPNA, ssPNA, pcPNA and the like) or locked nucleic acid (LNA) molecules. In still other embodiments, the unit specific markers are peptides or polypeptides. In still another embodiment, the polymer is composed of a backbone, which optionally includes a label (e.g., the backbone can include an inherent label or an extrinsic label).

In one embodiment, the unit specific markers have identical binding specificity. As an example, the unit specific markers may be nucleic acid molecules having an identical sequence. The length of the marker will depend upon the particular embodiment. Thus, in one embodiment, a marker that is a nucleic acid molecule is less than 12 bases in length, while in another embodiment, the marker that is a nucleic acid molecule is at least 4 bases in length.

In certain embodiments, the first and second unit specific markers (as well as any subsequent unit specific markers) are conjugated to a label, preferably a detectable label. In some embodiments, the label is selected from the group consisting of an electron spin resonance molecule, a fluorescent molecule, a chemiluminescent molecule, a radioisotope, an enzyme substrate, an enzyme, a biotin molecule, an avidin molecule, an electrical charge transferring molecule, a semiconductor nanocrystal, a semiconductor nanoparticle, a colloid gold nanocrystal, a ligand, a microbead, a magnetic bead, a paramagnetic molecule, a quantum dot, a chromogenic substrate, an affinity molecule, a protein, a peptide, a nucleic acid, a carbohydrate, a hapten, an antigen, an antibody, an antibody fragment, and a lipid.

In some embodiments, the first, second and subsequent labels are independently selected from the above group of labels.

In related embodiments, the signals produced from the labels are detected using a detection system. The detection system may be non-electrical in nature (such as a photographic film detection system), or it may be electrical in nature (such as a charge coupled device (CCD) detection system), but is not so limited. In some embodiments, the detection system is selected from the group consisting of a charge coupled device detection system, an electron spin resonance (ESR) detection system, a fluorescent detection system, an electrical detection system, an electromagnetic detection system, a photographic film detection system, a chemiluminescent detection system, an enzyme detection system, an atomic force microscopy (AFM) detection system, a scanning tunneling microscopy (STM) detection system, an optical detection system, a nuclear magnetic resonance (NMR) detection system, a near field detection system, and a total internal reflection (TIR) detection system.

In another aspect, the invention provides a system for optically analyzing a polymer of linked units comprising (a) an optical source for emitting optical radiation of a known wavelength; (b) an interaction station for receiving the optical radiation in an optical path and for sequentially receiving units of the polymer that are exposed to the optical radiation to produce detectable signals; (c) dichroic reflectors in the optical path for creating at least two separate wavelength bands of the detectable signals; (d) optical detectors constructed to detect radiation including the signals resulting from interaction of the units with the optical radiation; and (e) a processor constructed and arranged to analyze the polymer based on the detected radiation including the signals.

Preferably, the units of the polymer are bound to unit specific markers which in turn are labeled. In such embodiments, the signal derives from the label.

In one embodiment, the units of the polymer are labeled either directly or indirectly (e.g., with a labeled unit specific marker) with at least two radiation sensitive labels. In another embodiment, the units of the polymer are labeled with at least two radiation insensitive labels. Examples of useful labels include labels that have a size dependent feature to them, labels that comprise a particular chemical group, etc. Those of ordinary skill in the art will be familiar with examples of both categories.

In another aspect, the invention provides a system for optically analyzing a polymer. This system comprises an optical source for emitting optical radiation; an interaction station for receiving the optical radiation and for receiving a polymer that is exposed to the optical radiation to produce detectable signals; and a processor constructed and arranged to analyze the polymer based on the detected radiation including the signals. As described above, the polymer is bound to at least two unit specific markers that are preferably labeled.

In one embodiment, the interaction station includes a localized radiation spot. In a further embodiment, the system further comprises a microchannel that is constructed to receive and advance the polymer units through the localized radiation spot, and which optionally may produce the localized radiation spot. In another embodiment, the system further comprises a polarizer, and the optical source includes a laser constructed to emit a beam of radiation. The polarizer may be arranged to polarize the beam. While laser beams are intrinsically polarized, certain diode lasers would benefit from the use of a polarizer. In some embodiments, the localized radiation spot is produced using a slit located in the interaction station. The slit may have a slit width in the range of 1 nm to 500 nm, or in the range of 10 nm to 100 nm. In another embodiment, the interaction station includes a microchannel and a slit having a submicron width arranged to produce the localized radiation spot. In some embodiments, the polarizer is arranged to polarize the beam prior to reaching the slit. In other embodiments, the polarizer is arranged to polarize the beam in parallel to the width of the slit. The foregoing embodiments apply equally to other aspects of the invention.

In yet another embodiment, the optical source is a light source integrated on a chip. Excitation light may also be delivered using an external fiber or an integrated light guide. In the latter instance, the system would further comprise a secondary light source from an external laser that is delivered to the chip.

In yet another aspect, the invention provides a method for analyzing a polymer of linked units comprising generating optical radiation of a known wavelength to produce a localized radiation spot at a microchannel to define a detection station having a known detection resolution; labeling the polymer with first and second unit specific markers, the first unit specific marker including a first label and the second unit specific marker including a second label distinct from the first label, wherein the markers are spaced apart on the polymer such that, if the labels were not distinct from each other, they would be separated by a distance less than the detection resolution; sequentially exposing the first and second labels to the localized radiation spot; sequentially detecting radiation of at least two distinct wavelength bands resulting from interaction of the first and second labels with the localized radiation spot; and analyzing the polymer using the detected wavelength bands. In one embodiment, the method further comprises providing the microchannel.

In one embodiment, the method further comprises applying an electric field to move the polymer through the microchannel. In another embodiment, the method further comprises applying pressure to move the polymer though the microchannel. In yet another embodiment, the method further comprises applying suction to move the polymer through the microchannel. In another embodiment, the detecting includes collecting the signals over time while the unit specific markers are passing through the microchannel.

In one embodiment, the first and second labels are independently selected from the group of labels listed above.

In one embodiment, detecting includes collecting the first and second signals arising from the first and second labels while the first and second unit specific markers are moving through the microchannel.

In one embodiment, the first unit specific marker is different from the second unit specific marker. In another embodiment, the first unit specific marker is identical to the second unit specific marker. In an important embodiment, the first and second unit specific markers are nucleic acid molecules. In a related embodiment, the first and second unit specific markers are peptide nucleic acid molecules or locked nucleic acid molecules. In one embodiment, the first and second unit specific markers have an identical nucleotide sequence. In other embodiments, the first and second unit specific markers have identical binding specificities (i.e., they recognize and bind to the same polymer unit (or sequence) with the same affinity). It is to be understood that generally only one marker will be bound to one unit at a given time. In a related embodiment, the first and second unit specific markers are at least 4 bases in length. In another embodiment, the first and second unit specific markers are less than 12 bases in length.

In one embodiment, the first unit specific marker and the second unit specific marker are positioned immediately adjacent to one another. In another embodiment, first unit specific marker and the second unit specific marker are spatially separated from one another by at least two units.

In one embodiment, the polymer is labeled with a third unit specific marker, preferably comprising a third label. In a related embodiment, the third unit specific marker is spaced apart from the first and second unit specific markers by a distance greater than the known detection resolution (i.e., the minimum detection resolution).

In other embodiments, the signals are detected using a detection system of either electrical or non-electrical nature, such as those listed above.

In one embodiment, the polymer is a nucleic acid molecule. In some embodiments, the polymer is genomic DNA or RNA. In certain embodiments, the polymer comprises a backbone that includes a label.

In some embodiments, the first and second unit specific markers are nucleic acid molecules.

In some embodiments, the first and second unit specific markers are peptide nucleic acid molecules or locked nucleic acid molecules.

In some embodiments, the first and second unit specific markers have an identical nucleotide sequence.

In some embodiments, the first and second unit specific markers are less than 12 bases in length. And in some embodiments, the first and second unit specific markers are at least 4 bases in length.

In the various aspects of the invention, the pattern of binding of the unit specific markers to the polymer, and/or the signals derived from such markers may be determined using a variety of systems including a linear polymer analysis system. In some embodiments, the linear polymer analysis system is a single polymer analysis system. The nucleic acid molecule or the binding of the tag molecule to the nucleic acid molecule can be analyzed using a method selected from the group consisting of Gene Engine™, optical mapping, and DNA combing. The Gene Engine™ system is described in published PCT Patent Applications WO98/35012, WO00/09757 and WO01/13088, published on Aug. 13, 1998, Feb. 24, 2000 and Feb. 22, 2001 respectively, and in U.S. Pat. No. 6,355,420 B1 issued on Mar. 12, 2002, all of which are incorporated herein by reference in their entirety. Alternatively, the pattern may be determined using fluorescence in situ hybridization (FISH). Those of skill in the art will be aware of other systems that can be employed to determine the pattern of binding of the unit specific markers to the polymer.

In still another aspect, the invention provides a method for analyzing a polymer comprising labeling a polymer with a set of unit specific markers, wherein each unit specific marker of the set of unit specific markers recognizes and binds to units of identical sequence within the polymer. Each unit specific marker is labeled with one of at least two distinct labels. The method further comprises detecting signals arising from the labels to analyze the polymer. The set of unit specific markers can be at least two, at least 3, at least 4, or more unit specific markers.

In one embodiment, about 50% of the unit specific markers are labeled with a first label and about 50% of the unit specific markers are labeled with a second label. As used in this context, "about 50%" preferably means 35%-65%, 40%-60%, 45%-55%, or 47%-53% and 49%-51%. In other embodiments, it preferably includes 35%, 37%, 40%, 42%, 45%, 47%, 48%, 49%, 50%, 51%, 52%, 53%,55%, 57%, 60%, 63% and 65%. In another embodiment, each unit specific marker is labeled with one of at least three distinct labels. In yet another embodiment, each unit specific marker is labeled with one of at least four distinct labels.

In one embodiment, the unit specific markers have identical sequence. In another embodiments, the unit specific markers are greater than 4 nucleotides in length or less than 12 bases in length.

In other embodiments, the labels are of a type selected from the group listed above.

These and other aspects of the invention will be described in greater detail herein.

Each of the aspects of the invention can encompass various embodiments of the invention. It is therefore anticipated that each of the embodiments of the invention involving any one element or combinations of elements can be included in each aspect of the invention.

Figure 1:
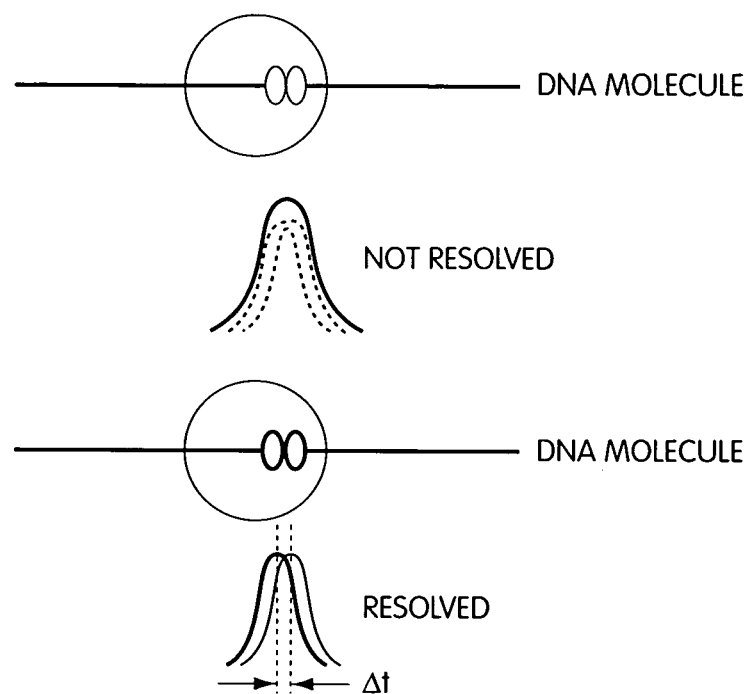
FIG. 1 is a schematic representation illustrating the effect of unit specific markers conjugated with different labels versus unit specific markers conjugated with identical labels on spatial resolution. When both unit specific markers are conjugated with the same label (e.g., a green fluorescent molecule), the signal from either cannot be resolved over the other. However, when the unit specific markers are conjugated with different labels (e.g., one with a green fluorescent molecule and the other with a red fluorescent molecule), the signal from either can be resolved over the other. In addition, the Figure indicates that the time between the distinguishable signal peaks (achievable when different labels are used) is indicative of the distance between the position of the unit specific markers on the polymer.

It is to be understood that the drawings are not required for enablement of the claimed invention.

DETAILED DESCRIPTION OF THE INVENTION

Aspects of the invention relate to systems and methods for achieving high-resolution linear analysis of polymers using differential tagging. Linear analysis of a polymer often requires a high-resolution reading of sequence-specific tags. However, the relative spacing of these sequence-specific tags may be below the resolution of the detection system. In response to this limitation, the invention provides a method that enables higher resolution in a given detection system by differentially tagging the linear polymer with distinguishable sequence-specific tags and capturing the differential signals arising from these tags along the length of the polymer. As a result of this differential tagging approach, two or more distinct tags (or as used herein, unit specific markers) that are in close proximity to each other can be distinguished and thus identified as separate, regardless of whether the distance between them is below the detection resolution previously achievable using prior art detection systems and approaches. This allows the location of unit specific markers (and the units to which they correspond) to be mapped with greater positional certainty than was previously possible.

The nucleic acid molecules can be analyzed using linear polymer analysis systems. A linear polymer analysis system is a system that analyzes polymers in a linear manner (i.e., starting at one location on the polymer and then proceeding linearly in either direction therefrom). As a polymer is analyzed, the detectable labels attached to it (either directly or indirectly) are detected in either a sequential or simultaneous manner. When detected simultaneously, the signals usually for an image of the polymer, from which distances between labels can be determined. When detected sequentially, the signals are viewed in histogram form (signal intensity vs. time), that can then be translated into a map, with knowledge of the velocity of the nucleic acid molecule. It is to be understood that in some embodiments, the nucleic acid molecule is attached to a solid support, while in others it is free flowing. In either case, the velocity of the nucleic acid molecule as it moves past, for example, an interaction station or a detector, will aid in determining the position of the labels, relative to each other and relative to other detectable markers that may be present on the nucleic acid molecule.

Two general classes of linear analysis, namely fixed molecule and moving molecule linear analyses, have been described in that art. Linear analysis of fixed molecules has been described in the art and includes methods of fluid-fixing linear molecules such as DNA to surfaces and using imaging or scanning-based approaches to collect sequence information. Linear analysis of moving molecules employing either flow or electrophoretic systems has been described in the art, as discussed below.

An example of a linear polymer analysis system is the Gene Engine™ system described in PCT patent applications WO98/35012 and WO00/09757, published on Aug. 13, 1998, and Feb. 24, 2000, respectively, and in issued U.S. Pat. No. 6,355,420 B1, issued Mar. 12, 2002. The contents of these applications and patent, as well as those of other applications and patents, and references cited herein are incorporated by reference in their entirety. This system allows single polymers such as single nucleic acid molecules to be passed through an interaction station in a linear manner. In the case of nucleic acid molecules, the nucleotides in the nucleic acid molecules are interrogated individually in order to determine whether there is a detectable label conjugated (e.g., via a unit specific marker) to the nucleic acid molecule. The detectable label preferably gives rise to the signal detected. Interrogation involves exposing the nucleic acid molecule to an energy source such as optical radiation of a set wavelength. In response to the energy source exposure, the detectable label emits a detectable signal. The mechanism for signal emission and detection will depend on the type of label sought to be detected.

Other single molecule nucleic acid analytical methods which involve elongation of DNA molecule can also be used in the methods of the invention. These include optical mapping (Schwartz et al., 1993; Meng et al., 1995; Jing et al., 1998; Aston, 1999) and fiber-fluorescence in situ hybridization (fiber-FISH) (Bensimon et al., 1997). In optical mapping, nucleic acid molecules are elongated in a fluid sample and fixed in the elongated conformation in a gel or on a surface. Restriction digestions are then performed on the elongated and fixed nucleic acid molecules. Ordered restriction maps are then generated by determining the size of the restriction fragments. In fiber-FISH, nucleic acid molecules are elongated and fixed on a surface by molecular combing. Hybridization with fluorescently labeled probe sequences allows determination of sequence landmarks on the nucleic acid molecules. Both methods require fixation of elongated molecules so that molecular lengths and/or distances between markers can be measured. Pulse field gel electrophoresis can also be used to analyze the labeled nucleic acid molecules. Pulse field gel electrophoresis is described by Schwartz et al. (1984). Other nucleic acid analysis systems are described by Otobe et al. (2001), Bensimon et al. in U.S. Pat. No. 6,248,537, issued Jun. 19, 2001, Herrick and Bensimon (1999), Schwartz in U.S. Pat. No. 6,150,089 issued Nov. 21, 2000 and U.S. Pat. No. 6,294,136, issued Sep. 25, 2001. Other linear polymer analysis systems can also be used, and the invention is not intended to be limited to solely those listed herein.

If confocal laser illumination is used in the analysis of a moving molecule (e.g., flow analysis of DNA) and the laser is operating in the TEMoo mode, then a Gaussian illumination pattern can be achieved and the emission of fluorescence from the probe (i.e., the unit specific marker) will vary to a certain extent according to the Gaussian profile of the illumination. This results in a non-uniform fluorescent signal as the probe traverses the detection spot. The fluorescent signal will manifest itself as a peak as the probe passes through the region of highest excitation intensity. When the resulting temporal pattern of fluorescence signals is examined, the relative location of adjacent probes on the target can be resolved to better than the spot size by using the peak output to locate the probe on the target. This is limited however to probes that are spatially separated sufficiently so that two temporally resolved peaks are present in the detected signal. This creates a minimum resolvable spatial probe separation, or as referred to herein, the known detection resolution.

Aspects of the present invention provide a system that overcome this limitation in spatial separation by analyzing polymers using differentially labeled unit specific markers. The method involves analyzing a polymer by identifying the presence and/or position of labeled unit specific markers bound along its length. Information can be obtained about the structure of the polymer including its size, the order of its units (e.g., its sequence), the repetition of its units (e.g., its complexity), its relatedness to other polymers, or its presence in a biological sample. For instance, the presence of a marker on a polymer can reveal the identity of the polymer.

One of the discoveries of the present invention is the finding that the first and second unit specific markers can be positioned within the known detection resolution limit of prior art detection methods and systems and can still be distinguished from each other and thereby detected individually. This results in greater mapping or sequence resolution. As used herein, the term "known detection resolution" refers to the closest distance that two markers having the same label can be positioned relative to each other and still be individually detectable and thus resolvable as two separate markers, using prior art methods. As will be explained in greater detail below, the known detection resolution of prior art fluorescence systems is generally $\lambda/2$ (i.e., half the emitted wavelength of the detectable signal). Thus, for systems in which all the fluorescent labels emit at 532 nm for example, the spatial resolution is 532 nm/2 or 266 nm, which approximates the distance of 782 base pairs. Accordingly, sequence information could only be achieved at intervals of approximately 782 base pairs on average using single color detection systems.

Using the systems and methods provided herein, it is possible to spatially resolve first and second unit specific markers when these are located at a distance less than the known detection resolution. This distance is referred to herein as "below known detection resolution". The system detection resolution limits that could be achieved prior to the present invention vary with the type of system. As described herein, an optical detection system such as a fluorescence system has a resolution limit of λ/2 without using the differential tagging approach described herein. Accordingly, the "below known detection resolution" for optical detection systems is less than λ/2, where λ represents the emission wavelength characteristic of a single color system. FIG. 1 illustrates the result of using two markers having the same label and two probes having different labels on spatial resolution. Known detection resolutions for other detection modalities are known in the art.

While in its simplest form this method involves two distinguishable unit specific markers, it is possible that additional unit specific markers are used, provided that they too are distinguishable from the first and second unit specific markers. The third and subsequent unit specific markers may be positioned relative to the first and second unit specific markers such that the signal produced by the third and subsequent unit specific marker is above the known detection resolution with respect to the signals of the first and second unit specific markers. As used herein, "above known detection resolution" is greater than λ/2, for optical detection systems.

The methods provided herein are capable of generating signatures for each polymer based on the specific interactions between unit specific markers and polymers. A signature is the signal pattern that arises along the length of a polymer as a result of the binding of unit specific markers (of different or identical sequence) to the polymer. The signature of the polymer uniquely identifies the polymer.

One type of analysis embraced by the methods described herein involves analyzing patterns of hybridization of two or more unit specific markers to individual polymers. The methods of the invention can identify unknown expressed genes by computer analysis of the hybridization patterns generated. The data obtained from linear analysis of the DNA unit specific markers are then matched with information in a database to determine the identity of the target DNA. The methods can thus analyze information from hybridization reactions, which can then be applied to diagnostics and determination of gene expression patterns.

Figure 9:
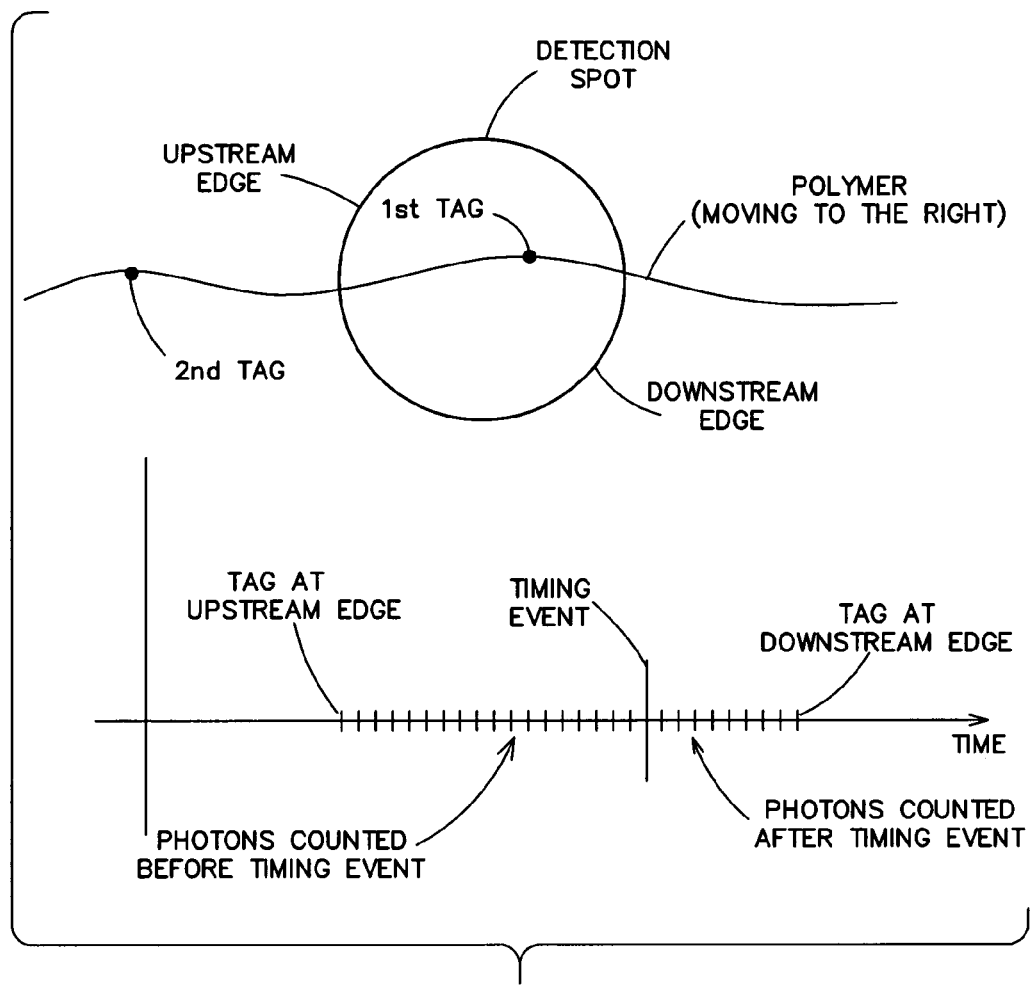
FIG. 9 is a schematic representation of a polymer with a first and second tag passing through the detection spot of a detection system. The first tag is shown in the detection spot and the second tag has not yet entered the detection spot. In the lower portion of the Figure, a time dependent photon count from the detection spot is shown. This time dependent signal includes photons that were detected from the first tag prior to the timing event, which occurs at the time represented in the upper portion of the Figure. It also includes photons detected from the first tag after the timing event.

Other aspects of the invention are related to improving the precision of separation distance measurements in the analysis of polymers, either when the separation distance is below or within the known detection resolution. In one embodiment, a tagged polymer is linearized and forced through a channel. A laser is directed to a detection spot within the channel. As the tags of the polymer pass through the detection spot, the laser causes them to fluoresce. The photons emitted from the fluorescing tags are collected and continuously counted by the detection system from the time they enter the detection spot until they exit the detection spot. The photon count restarts at a timing event, which occurs when the first tag is in the detection spot. This provides a first count of photons emitted by the first tag in the detection spot before the timing event and a second count of photons emitted by the first tag in the detection spot after the timing event. FIG. 9 is a schematic representation of such an occurrence. When added, the first and second counts define a total photon count for the first tag. The first photon count is compared to the total photon count to determine the position of the first tag, relative to the upstream edge of the detection spot, when the timing event occurred.

This is accomplished using Equation 1 below to identify the distance between the first tag and the upstream edge of the detection spot at the timing event. In this manner, this method provides an estimate of tag position with a precision that is greater than the width of the detection spot.

$$b = ws \frac{b_1}{(b_1 + b_2)} \quad \text{[Equation 1]}$$

where:
b=distance between first tag and upstream edge of the detection spot at the timing event
ws=window size
$b_1$ =first tag photon count before the timing event
$b_2$ =first tag photon count after the timing event The position of a second tag passing through the detection spot is estimated in a manner similar to the first tag, as illustrated in FIG. 9. This is represented below by Equation 2. Variables "b" and "r" are used in Equations 1 and 2 to represent that the photons emitted by the first and second tags might be within the blue and red spectrums, respectively. However, the first and second tags are not limited to tags that emit these types of photons, or to any particular tags as the invention is not limited in this respect. Similarly, the first and second tags may also be the same type of tag, as aspects of the present invention can be applied to scenarios having both similar and dissimilar types of tags.

$$r = ws \frac{r_1}{(r_1 + r_2)} \quad \text{[Equation 2]}$$

where:
r=distance between second tag and upstream edge of the detection spot at the timing event
ws=window size
$r_1$ =photon count from second tag before the timing event
$r_2$ =photon count from second tag after the timing event The estimated position of the second tag at the timing event is then subtracted from the estimated position of the first tag at the timing event to define separation distance between the first and second tag. This calculation is represented by Equation 3.

$$\text{separation\_distance} = r - b + rv*et \quad \text{[Equation 3]}$$

where:
separation_distance=separation distance between the first and second tags
b=distance between first tag and upstream edge of detection spot at the timing event
r=distance between first tag and upstream edge of detection spot at the timing event
rv=relative velocity between polymer and detection spot
et=elapsed time between timing events associated with the first and second tags In cases where the positions of the first and second tags are measured at different timing events, a distance corresponding to how far the polymer traveled between the timing events is added to compensate for the relative movement of the polymer with respect to the detection spot between the timing events. This distance is calculated by multiplying the time elapsed between the timing events by the average relative velocity between the detection spot and the polymer. These calculations are also represented by Equation 3.

Figure 10:
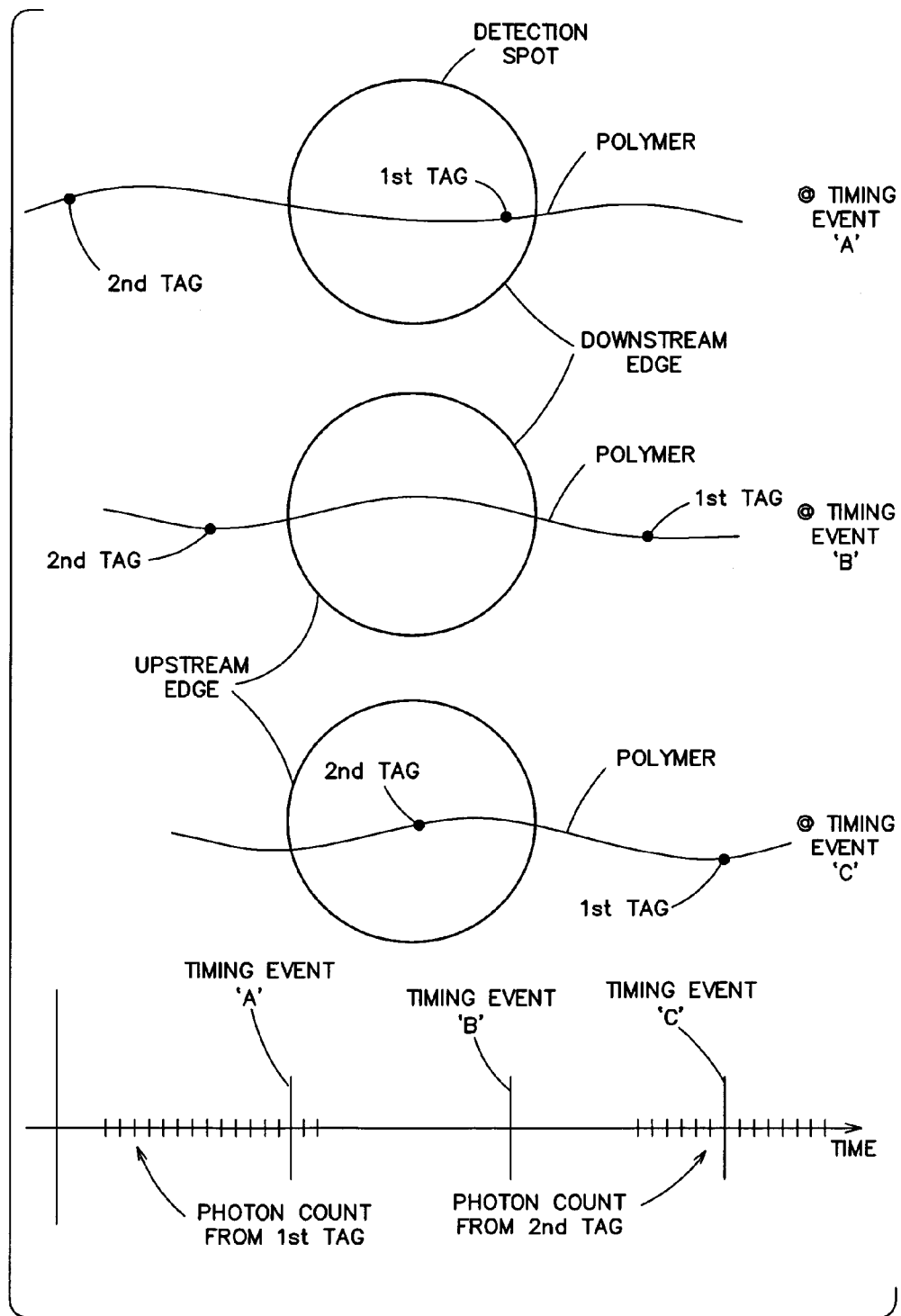
FIG. 10 is a schematic representation, at three different timing events, of a polymer with a first and second tag passing through a detection spot. The corresponding photon count from the detection spot is shown in the lower portion of the Figure. Here, the photon count includes hash marks labeled 'A', 'B', and 'C' that indicate when the corresponding timing events occurred.

FIG. 10 shows an example of the above described scenario. Here, a polymer having a first and second tag passes through a detection spot. While the first tag is present in the detection spot and is emitting photons, a first timing event occurs. As the first tag of the polymer passes the downstream edge of the detection spot, the first tag quits emitting photons. After the first tag has passed through the detection spot, but the before the second tag has passed the upstream edge of the detection spot, a second timing event occurs. Subsequently, the second tag passes the upstream edge of the detection spot and begins emitting photons that are collected by the detection system. When the second tag has passed about half-way through the detection spot, a third timing event occurs. In this scenario, Equations 1 and 2 are used to calculate the distance between the first and second tags from the upstream edge of the detection spot at the first and third timing events, respectively. To compensate for the fact that each of these measurements is taken at different timing events, the time elapsed between the first and third timing events is multiplied by the average velocity of the polymer through the detection spot. The resulting value is added to the difference of the first tag and the upstream edge at the first timing event and the distance between the second tag and the upstream edge of the detection spot at the third timing event.

Aspects of the invention are often used in detection systems that regularly bin data. "Binning" as used herein describes the technique of dividing data acquired over a larger time (or space) into smaller components for analysis. Binning may occur while a detection signal is gathered in a detection system, or binning may occur as an analysis step applied to a detection signal that was previously gathered by a detection system. In the above described embodiment, photons are collected from tags passing through the detection spot over time. Timing events occur periodically, separated by a common reset time that divides the photon counts collected from the detection spot into a sequence of bins. In this manner, binning provides a series of photon counts from regularly spaced time intervals.

"Bin size" as used herein describes the distance that a sample travels during a given time period, namely the reset time. Bin size is indicative of the amount of information that a given bin contains and is defined by multiplying the reset time by the relative velocity between the polymer and the detection spot, as shown in Equation 4. "Reset time" as used herein is the time elapsed between adjacent timing events. "Window size" as used herein is the average distance across a detection spot. Also, as used herein, "relative velocity" refers to the velocity of the polymer between the upstream and downstream edges of the detection spot.

$$\text{bin\_size} = \text{reset\_time} * \text{relative\_velocity} \quad \text{[Equation 4]}$$

Reset time, window size, and the relative velocity are each factors that affect the amount of information contained in a given bin. Additionally, each of these factors can be adjusted to some degree to impact the quantity and/or quality of the information in each bin. In most embodiments, the reset time is adjusted so that a portion of a polymer that just enters the detection spot at a first timing event is also just exiting the detection spot at the next timing event. To accomplish this, reset time is set such that it equals the window size divided by the relative velocity, as shown by Equation 5. In detection systems with bin size set in this manner, a tag can influence at most two adjacent bins.

$$\text{reset\_time} = \text{window\_size} / \text{relative\_velocity} \quad \text{[Equation 5]}$$

Reset time is the time elapsed between adjacent timing events, which define the beginning and end of a bin, respectively. In most embodiments, reset time is a constant value for the detection system. However, the reset time can be variable as the invention is not limited in this respect. A longer reset time will result in bins that each cover a greater period of time, and fewer bins within a given total amount of analysis time. All else constant, a given bin will count more photons from a given tag in a system with a longer reset time. Having more photons in any given bin for each given tag can improve the quality of detection signals by increasing the strength of the detection signals relative to the system noise level. However, on the other hand, longer reset times also increases the probability of multiple tags contributing photons to the same bin, which can cause uncertainties in analysis if the tags are not distinguishable from one another. Additionally, when reset times are longer than the window size divided by relative velocity, the possibility exists that all of the photons emitted by a tag will be collected in a single bin. In such a scenario, if the reset time is only slightly greater than the window size divided by relative velocity, the tag can be estimated to be located near the portion of the polymer that entered the detection spot at the timing event. However, when the reset time is significantly greater than window size divided by relative velocity, the reduction in precision of the estimated location can also be significant.

Relative velocity is another factor that affects the amount of information within a given bin. For example, a polymer moving faster relative to a detection spot will reside within the detection spot for a shorter period of time and any tags on the polymer will emit fewer photons as they pass through the detection spot. It is generally preferred to receive more photons from any given tag to help distinguish detection signals from the noise level of the system. As such, a slower relative velocity is generally preferred for detection signal quality reasons. However, a slower relative velocity generally means that the overall analysis will take longer to complete. Since it is preferable to complete the analysis in a shorter timeframe, there is typically a tradeoff between relative sample velocity, which directly impacts the speed at which the detection system may operate, and the quality of the data collected (i.e., the strength of the signal collected relative to the noise level in the system).

Quite often, other factors in a detection system dictate the velocity at which the sample moves relative to the detection spot. As such, relative velocity is not typically a factor that is optimized when the detection system is designed. Rather, other factors, such as reset time and potentially window size are adjusted to accommodate the required relative velocity between the sample and the detection spot. As an example, in many microfluidic analysis systems, the fluid carrying the polymer may only travel within a range of velocities without causing adverse effects on the sample or system. In such systems, an operator typically adjusts reset time and window size to impact the amount of information and signal strength within any given bin of the data stream, instead of adjusting the relative velocity.

Window size is yet another factor that affects the amount and quality of data in the bins of a data stream. As mentioned above, window size is the average distance across a detection spot, measured typically in microns. The distance is taken in the direction of relative movement between the sample and the detection spot, regardless of which of the two is actually moving. A larger window size generally increases the amount of information provided to any bin of a data stream, all else constant. For example, where a detection spot and thus window size is larger, a sample will reside within the detection spot for a longer period of time as it moves through the spot. As such, the detection system with a larger window size will detect more photons for a given tag. As discussed above, having more photons from a given tag generally improves the quality of the signal, as it diminishes the effects of noise on the detection system. However, increasing the window size of a detection spot also increases the probability that more than one tag will be resident in the detection spot at the same time, which can confuse the analysis. Although distinct tags can be distinguished when in the detection spot together, similar tags may cause uncertainties in some detection systems.

As with relative velocity, outside factors may dictate an acceptable window size or range of acceptable window sizes. Some detectors may have an optimal focus size, where deviating from the optimal size reduces the detection efficiency of the detection system. In other embodiments, the geometry of the interaction station may dictate the size of the detection spot. For instance, systems having large interaction stations may require a larger detection spot to cover the entire area where a polymer may pass.

To help minimize the impact of system noise on the detection system, some embodiments require a threshold level of photons to be collected within a given bin before any photons are acknowledged and recorded. The threshold level is set at or above the noise level of the system to prevent noise from inadvertently being interpreted as the presence of a tag. In some of these embodiments, the photons emitted within the detection spot, both within a period of time just before and after the timing event are counted in both of the bins before and after the timing event. Counting photons in this manner can prevent ambiguities associated with tags whose photons might otherwise only be detected in one bin, such as in systems that have a threshold level and have reset time set equal to or greater than window size divided by relative velocity.

Some detection systems convert binned data into a barcode. A barcode is created from the binned data by assigning numbers to bins according to what type of signal, and/or how many photons a given bin contains. For instance, a zero may be assigned to any bin where the number of photons collected is below a predetermined threshold level. Similarly, any bin having a photon count above the threshold level for a first type of tag may be assigned a one (1). Bins having photon counts above a threshold level for a second type of tag may be assigned a two (2) while bins having photon counts above the threshold levels for both the first and second tags, respectively, may be assigned a three (3).

In systems where reset time is set equal to window size divided by relative velocity, each non-zero barcode value will generally be adjacent to at least one other non-zero value. Each pair of adjacent non-zero values indicate a point where one or more tags were present when a timing event occurred. The methods described above can be applied to the photon counts at each of these points to determine, more precisely, the location of each tag at the respective timing event. Knowledge of the reset time between each timing event and the relative velocity, can then be used to convert binned data or the barcode into data that represents the separation between each of the tags on the polymer. This data can also be used to determine the separation distance between the tags and the beginning and/or end of the polymer when the beginning and end are also detected by the system. This may be accomplished in some embodiments through the use of a detectable intercalating dye placed on the backbone of the sample.

Figure 11:
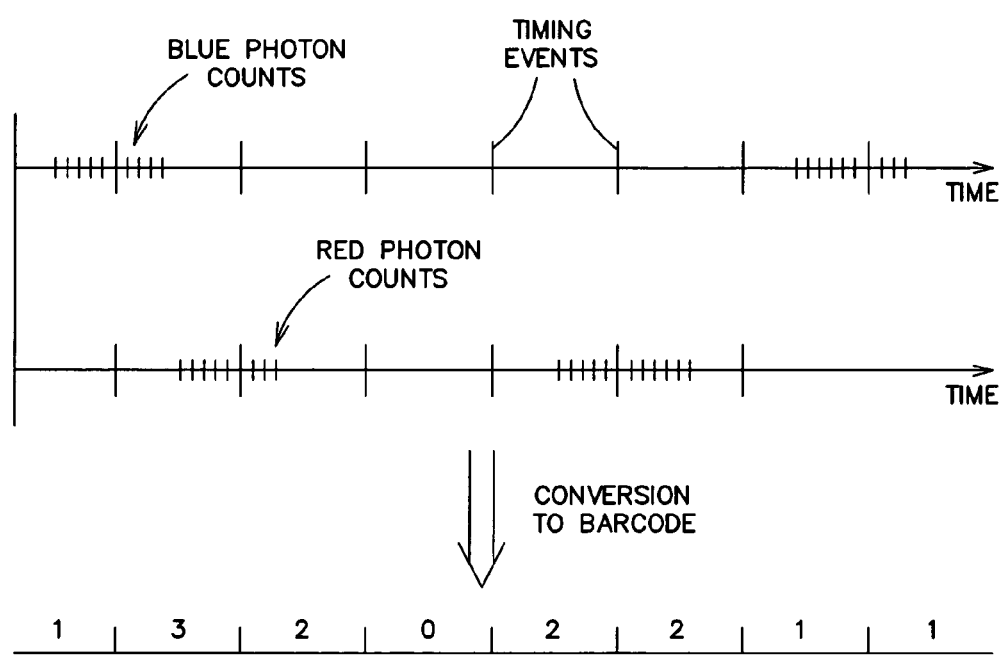
FIG. 11 is a schematic representation of photon counts for a blue tag on a polymer that passes through a detection spot and a red tag on a polymer that passes through the detection spot. Each of these photon counts are shown as separate time dependent signals. Beneath the time dependent signals is a barcode created from the photon count data.

FIG. 11 depicts how binned data can be converted into a barcode. In this Figure a time dependent photon count for a blue tag and a corresponding time dependent photon count for a red tag are shown. Resulting barcode values for each of the bins is reflected beneath these photon counts. As can be seen, each of the non-zero barcode values is adjacent to at least one other non-zero value. Timing events are also interposed on the time varying photon counts. Each of these timing events correspond to boundaries between the bins and thus boundaries between each of the barcode values. The resulting barcode can be used to define the position of a given tag relative to other tags, the beginning or end of the polymer, and/or the upstream edge of the detection spot at the respective timing event.

Intrinsic randomness in detection systems also affects the accuracy and the precision of most detection systems. However, aspects of the present invention help reduce the effects of much of this intrinsic randomness, further improving the precision of resulting separation distance measurements. In particular, they help reduce the effects of variability of the total photon count for any single tag, which is often affected by variability in the orientation of the tag relative to the laser and/or detector. Laser spots used in detection systems are often more intense near their center, and less intense near their periphery. Tags in the more intense portion of the laser spot typically emit a greater number of photons. This means that a tag passing across the detection spot center will generally produce a greater total photon count than a tag passing across a non-central portion of the detection spot. However, the fact that the total photon count is lower does not affect the precision of the measurement in this scenario because the total photon count for the tag is affected evenly, and thus falls out of Equation 1 or 2 which rely on proportions of total photons rather than absolute photon counts to estimate the distance between the tag and the upstream edge of the detection spot. This same argument would cancel out differences caused by fluorescent variability across tags.

Figure 12:
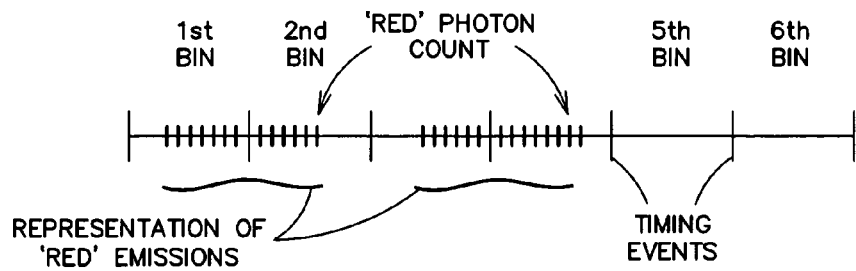
FIG. 12 is a schematic representation of a first scenario where aspects of the present invention may be used.

There are four primary types of scenarios where methods of the present invention are used within detection systems. In the first scenario, aspects of the present invention are used to determine the separation distance between two similar tags, each of which is detected in a pair of bins, none of which are common to both tags. This scenario is represented by FIG. 12, which depicts a polymer having two similar type tags. Also shown is a detection spot through which the polymer passes and a resulting time dependent photon count with timing events interposed. Here, photons emitted by each tag are present in adjacent bins. The position of each tag is estimated relative to the upstream edge of the detection spot when the respective timing event occurs, using Equation 1 or a mathematical equivalent. Separation distance is then estimated by using Equation 3, where the elapsed time is the time between the timing events that divide each of the pair of adjacent bins.

Figure 13:
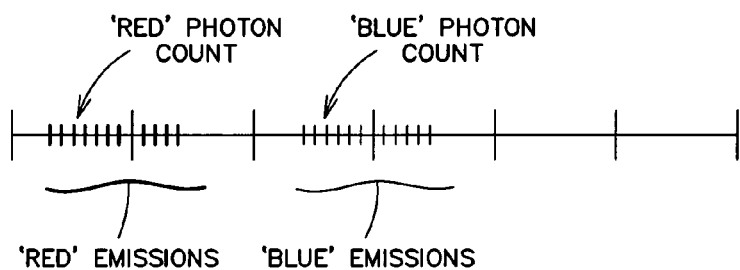
FIG. 13 is a schematic representation of a second scenario where aspects of the present invention may be used.

FIG. 13 represents a second scenario where methods of the present invention are used to estimate separation distance between two distinct types of tags on a polymer. This scenario is the same as that above in FIG. 13, except that the tags are different types, having emissions that are distinct from one another.

Figure 14:
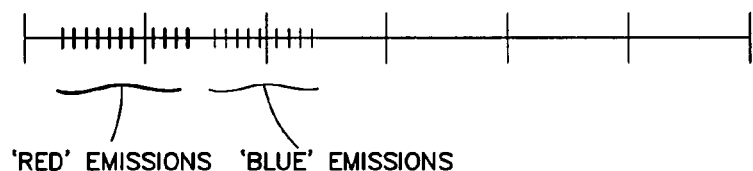
FIG. 14 is a schematic representation of a third scenario where aspects of the present invention may also be used.

FIG. 14 represents the third scenario, where two distinct tags are present on a polymer. In this scenario, the photon emissions from each tag are detected in one common bin and photons from each tag are also detected in one bin that is not common. As such, two separate timing events are used in determining the separation distance between the tags.

Figure 15:
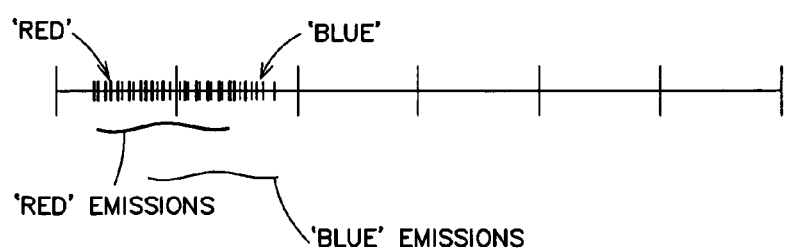
FIG. 15 is a schematic representation of a fourth scenario where aspects of the present invention may be used.

FIG. 15 represents the fourth scenario. Here, like in the third scenario, two distinct tags are present on a polymer. However, the photon emissions from each tag are collected within two common bins.

Although binning and various other aspects of the present invention were described above in the context of a sequential, linear polymer analysis system, many of the same aspects and methods of the invention are also applicable to other type systems. For instance, binning and other method of the present invention may also be used in simultaneous linear analysis systems.

A "polymer" as used herein is a compound having a linear backbone to which monomers are linked together by linkages. The polymer is made up of a plurality of individual monomers. An individual monomer as used herein is the smallest building block that can be linked directly or indirectly to other building blocks or monomers to form a polymer. At a minimum, the polymer contains at least two linked monomers. The particular type of monomer will depend upon the type of polymer being analyzed.

The term "backbone" is given its usual meaning in the field of polymer chemistry. The polymers may be heterogeneous in backbone composition thereby containing any possible combination of polymer monomers linked together. In a preferred embodiment the polymers are homogeneous in backbone composition and are, for example, nucleic acids, polypeptides, polysaccharides, carbohydrates, polyurethanes, polycarbonates, polyureas, polyethyleneimines, polyarylene sulfides, polysiloxanes, polyimides, polyacetates, polyamides, polyesters, or polythioesters.

As used herein with respect to linked monomers of a polymer, "linked" or "linkage" means two entities are bound to one another by any physicochemical means. Any linkage known to those of ordinary skill in the art, covalent or non-covalent, is embraced. Such linkages are well known to those of ordinary skill in the art. Natural linkages, which are those ordinarily found in nature connecting the individual monomers of a particular polymer, are most common. Natural linkages include, for instance, amide, ester and thioester linkages. The individual monomers of a polymer may be linked, however, by synthetic or modified linkages. Polymers in which monomers are linked by covalent bonds will be most common. The polymer may be branched, but preferably it is linear.

In preferred embodiments, the polymer is a biological molecule. As used herein, a biological molecule is a molecule that is found in, or is functional in, a biological environment such as a cell. In some embodiments, the polymer is a peptide or a nucleic acid. A "peptide" as used herein is a polymer comprised of linked amino acids. A "nucleic acid" as used herein is a polymer comprised of linked nucleotides, and includes deoxyribonucleic acid (DNA) or ribonucleic acid (RNA). DNA is a polymer comprised of a phosphodiester backbone composed of monomers of purines and pyrimidines such as adenine, cytosine, guanine, thymine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. RNA is a polymer comprised of a phosphodiester backbone composed of monomers of purines and pyrimidines such as those described for DNA except that uracil is substituted for thyinidine. DNA monomers may be linked to each other by their 5' or 3' hydroxyl group thereby forming an ester linkage. RNA monomers may be linked to each other by their 5', 3' or 2' hydroxyl group thereby forming an ester linkage. Alternatively, DNA or RNA monomers having a terminal 5', 3' or 2' amino group may be linked to each other by the amino group thereby forming an amide linkage. In some instances, the polymer is a peptide nucleic acid (PNA), or a locked nucleic acid (LNA). In some important embodiments, the unit specific marker is a PNA or a LNA, as described below.

Whenever a nucleic acid is represented by a sequence of letters it will be understood that the nucleotides are in 5'□3' order from left to right and that "A" denotes adenosine, "C" denotes cytosine, "G" denotes guanosine, "T" denotes thymidine, and "U" denotes uracil unless otherwise noted.

The nucleic acid molecules used as targets may be DNA (e.g., genomic DNA including nuclear and mitochondrial DNA), or RNA, or amplification products or intermediates thereof, including complementary DNA (cDNA). The nucleic acid molecules can be directly harvested and isolated from a biological sample (such as a tissue or a cell culture) without the need for prior amplification using techniques such as polymerase chain reaction (PCR). In related embodiments, the nucleic acid molecule is a fragment of a genomic nucleic acid molecule.

The polymers may be "native polymers" which are naturally occurring, or alternatively they may be non-naturally occurring polymers which do not exist in nature. The polymers typically include at least a portion of a naturally occurring polymer. The polymers can be isolated or synthesized de novo. For example, the polymers can be isolated from natural sources e.g. purified, as by cleavage and gel separation or may be synthesized e.g., (i) amplified in vitro by, for example, polymerase chain reaction (PCR); (ii) synthesized by, for example, chemical synthesis; (iii) recombinantly produced by cloning, etc. An example of an isolated polymer suitable for analysis using the methods described herein is genomic DNA harvested from a cell, tissue or subject.

The nucleic acid molecules may be single stranded and double stranded nucleic acids. Harvest and isolation of nucleic acid molecules are routinely performed in the art and suitable methods can be found in standard molecular biology textbooks (e.g., such as Maniatis' Handbook of Molecular Biology).

In important embodiments of the invention, the nucleic acid molecule is a non in vitro amplified nucleic acid molecule. As used herein, a "non in vitro amplified nucleic acid molecule" refers to a nucleic acid molecule that has not been amplified in vitro using techniques such as polymerase chain reaction or recombinant DNA methods. A non in vitro amplified nucleic acid molecule may however be a nucleic acid molecule that is amplified in vivo (in the biological sample from which it was harvested) as a natural consequence of the development of the cells in vivo. This means that the non in vitro nucleic acid molecule may be one which is amplified in vivo as part of locus amplification, which is commonly observed in some cell types as a result of mutation or cancer development.

The size of the nucleic acid molecule is not critical to the invention and it generally only limited by the detection system used. It can be several nucleotides in length, several hundred, several thousand, or several million nucleotides in length. In some embodiments, the nucleic acid molecule may be the length of a chromosome.

Peptides and polypeptides are polymers comprised of a peptide backbone composed of monomers of amino acids, which include the 20 naturally occurring amino acids as well as modified amino acids. Amino acids may exist as amides or free acids that are linked to each other and to the backbone through their □-amino group thereby forming an amide linkage. Amino acid designations as used herein correspond to the triplet or single letter designations that are commonly used in the art.

The methods of the invention are used to analyze polymers based on markers that recognize and bind to units within a polymer. A "unit" of a polymer, as used herein, refers to a particular linear arrangement of one or preferably more monomers (i.e., a particular defined sequence of monomers) within a target polymer. For example, a unit in a nucleic acid consists of a particular sequence of nucleotides linked to one another. A nucleic acid unit may consist of one, or two nucleotides (i.e., a dinucleotide or a 2-mer), or three nucleotides (i.e., a trinucleotide or a 3-mer), or four nucleotides (i.e., a tetranucleotide or a 4-mer), and so on. The unit may be of any length. As used herein, the polymer being analyzed using the methods of the invention is referred to as a "target polymer".

The units are identified within the polymer by the use of unit specific markers. "Unit specific markers" are molecules that specifically recognize and bind to particular units within a polymer in a sequence dependent manner. The terms "unit specific marker" and "marker" are used interchangeably herein. An example of a unit specific marker is a probe (e.g., a nucleic acid probe). The method of the invention comprises first labeling a polymer with at least two unit specific markers (such as for example, a first and a second unit specific marker). As used herein, a polymer that is bound by a unit specific marker is referred to as "labeled" with that unit specific marker. The position of the unit specific marker along the length of a target polymer indicates the location of a particular unit in the polymer. If a unit specific marker binds to a target polymer under conditions that favor specific binding, this indicates that the corresponding unit (and sequence) is present in the polymer. If a unit specific marker fails to bind to a target polymer under the same conditions, this generally indicates that the corresponding unit (and sequence) is not present in the polymer. It is to be understood that in the case of nucleic acid molecules, the sequences of the unit specific marker and the unit in the target nucleic acid are complementary to each other.

The unit specific marker may itself be a polymer but it is not so limited. Examples of suitable polymers are nucleic acid molecules (useful as unit specific markers for target polymers that are themselves nucleic acids) and peptides and polypeptides (useful as unit specific markers for target polymers that are nucleic acids and peptides). Other unit specific markers include but are not limited to sequence specific major and minor groove binders and intercalators, peptide binding proteins, nucleic acid binding peptides or polypeptides, and sequence-specific peptide-nucleic acids, etc. Many unit specific markers exist and are known to those of skill in the art. The unit specific marker can also be a PNA or a LNA.

Peptide nucleic acids (PNAs) are DNA analogs having their phosphate backbone replaced with 2-aminoethyl glycine residues linked to nucleotide bases through glycine amino nitrogen and methylenecarbonyl linkers. PNAs can bind to both DNA and RNA targets by Watson-Crick base pairing, and in so doing form stronger hybrids than would be possible with DNA or RNA based markers. Several types of PNA designs exist, and these include but are not limited to single strand PNA (ssPNA), bisPNA, pseudocomplementary PNA (pcPNA).

Peptide nucleic acids (PNA) are synthesized from monomers connected by a peptide bond (Nielsen and Egholm 1999). These can be built with standard solid phase peptide synthesis technology. PNA chemistry and synthesis also allows for inclusion of amino acids and polypeptide sequences in the PNA design. For example, lysine residues can be used to introduce positive charges in the PNA backbone. All chemical approaches available for the modifications of amino acid side chains are directly applicable to PNAs.

Locked nucleic acid (LNA) form hybrids with DNA, which are at least as stable as PNA/DNA hybrids (Braasch and Corey 2001). Therefore, LNA can be used just as PNA molecules would be. LNA binding efficiency can be increased in some embodiments by adding positive charges to the LNA marker. LNAs have been reported to have increased binding affinity inherently. Commercial nucleic acid synthesizers and standard phosphoramidite chemistry are used to make LNAs.

The unit specific marker can be of any length, as can the unit to which it binds. The length of the marker will depend upon the particular embodiment. The marker length may range from 2, 3, 4, 5, 6, 7, 8, 9, 10, 12, 15, 20, or more nucleotides (including every integer therebetween as if explicitly recited herein). In many embodiments, shorter markers are more desirable. In instances in which the polymer and the marker are both nucleic acids, the length of the unit and the unit specific marker are generally the same. This is not necessarily so if either or both the target polymer or the unit specific marker are not nucleic acids. The method embraces the simultaneous use of two or more unit specific markers that may be identical in nature or unit binding specificity. For example, the unit specific markers may recognize and bind specifically to identical units but they may themselves be different in their composition (e.g., one unit specific marker may be a nucleic acid and one may be a peptide). In some preferred embodiments, the unit specific markers are identical in their composition regardless of whether they recognize and bind specifically to identical units.

As stated above, the unit specific markers themselves may have identical binding specificity. Markers with identical binding specificity bind with the same affinity to units having the same sequence. Accordingly, these markers will bind with equal probability to their target units in the polymer, provided the label of the marker does not interfere with sequence recognition and binding of the marker to the unit.

In one embodiment of the invention, a set of unit specific markers all of which have identical binding specificity is used. Preferably the set of markers is divided into as many equal parts as possible, with each equal part labeled with a different label. For example, the set may be divided into two equal parts, one of which is labeled with a green fluorescent label (emitting at about 530 nm) and the other is labeled with a red fluorescent label (emitting at about 575 nm). As another example, the set may be divided into three equal parts, one of which is labeled with a green fluorescent label, one of which is labeled with a red fluorescent label, and the remaining one is labeled with a far-red fluorescent label (emitting at about 630 nm). The set may include at least 3, at least 4, at least 5, or more unit specific markers differentially labeled.

Alternatively, the unit specific markers may have different binding specificities. As used herein, markers with different binding specificities recognize and bind to different sequences (i.e., different units) in the target polymer. Unit specific markers recognizing and binding to a first unit may be labeled identically or they too may be differentially labeled, with the proviso that no single label is used to label markers for different sequences. This means that each signal arising from a labeled marker will denote only one unit or sequence along the length of the polymer.

In one important embodiment, the polymer being analyzed is a nucleic acid (i.e., a polymer of nucleotides), and the unit specific marker is another nucleic acid having a sequence that allows it to hybridize to the target polymer in a sequence specific manner. When the target polymer is a nucleic acid, the sequence of the unit specific marker will be complementary to the sequence of the unit to which it binds in the target polymer.

The first unit specific marker and the second unit specific marker may be but need not be positioned immediately adjacent (i.e., contiguous) to one another. As used herein, the term "positioned immediately adjacent to one another" means that no identical units are located between two units or in some instances, that no monomers are located between two units.

The position of units and markers along a target polymer will depend upon the length of the unit and the randomness of sequence distribution in the target molecule. For example, if the target unit comprises within its sequence a repetitive sequence (such as a poly-A sequence, an Alu repeat, or a CG dinucleotide), then it is more likely that the unit specific markers will be positioned relatively close to one another. If however the unit specific marker consists of 6 randomly selected nucleotides, then by chance there will be on average approximately 4096 bases between consecutive units along the length of the polymer.

The degree to which each target unit is bound by a unit specific marker will also depend upon the efficiency of binding (including the binding or hybridization conditions) and the concentration of the unit specific marker relative to the concentration of target polymer (and target units). If the binding efficiency is low or if the concentration of unit specific marker is not saturating, then the first and the second unit specific markers may be spatially separated from one another by one, two, three, or more units which will not be bound by unit specific markers.

The ability of the unit specific marker to bind specifically to its target unit will also depend upon its length and composition (particularly for markers that are nucleic acids) and the conditions under which interaction (i.e., binding) occurs. Unit specific markers will bind specifically to a unit of a particular sequence and not to units that differ in sequence from the target. If the polymer and the unit specific marker are both nucleic acids, the conditions can be manipulated so that only complementary sequences will bind to each other. Persons of ordinary skill in the art will know how to achieve and test for such stringent conditions. Reference can also be made to *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York for guidance in stringent hybridization conditions. If the unit specific marker is a peptide or polypeptide, the conditions are similarly manipulated so that only specific binding of the marker to a specific unit on the target polymer (which may be nucleic acid or peptide in nature itself) will occur. However, in some instances, binding conditions may be adjusted to allow the unit specific marker to bind to polymer units that are not completely complementary. This latter approach is useful when a less than exact sequence of the polymer is sought.

The unit specific markers are resolvable when located relative to each other at a distance less than the known detection resolution because they are differentially labeled. As used herein, "differentially labeled unit specific markers" are unit specific markers that are labeled (e.g., conjugated) with different labels that emit different and distinct signals.

A "label" as used herein is a molecule or compound that can be detected by a variety of methods including fluorescence, electrical conductivity, radioactivity, size, and the like. The label may be intrinsically capable of emitting a signal, such as for example fluorescent label that emits light of a particular wavelength following excitation by light of another lower, characteristic wavelength. Alternatively, the label may not be capable of intrinsically emitting a signal but it may be capable of being bound by another compound that does emit a signal. An example of this latter situation is a label such as biotin which itself does not emit a signal but which when bound to labeled avidin or streptavidin molecules can be detected. Other examples of this latter kind of label are ligands that bind specifically to particular receptors. Detectably labeled receptors are allowed to bind to ligand labeled unit specific markers in order to visualize such markers. Other label types are recited more fully herein.

The label produces a characteristic signal following interaction with an energy source such as a laser beam of a given wavelength (or range of wavelengths), or a current. While it is possible that either the target polymer or the unit specific marker are intrinsically labeled, it is preferable to use extrinsically labeled unit specific markers in the methods described herein. The type of extrinsic label selected will depend on a variety of factors, including the nature of the analysis being conducted, the type of the energy source used and the type of polymer. Extrinsic label compounds include but are not limited to light emitting compounds, electron emitting or absorbing compounds, spin labels, and heavy metal compounds. The label should be sterically and chemically compatible with the units of the polymer being analyzed, and with the unit specific markers used. The extrinsic label should not interfere with the binding of the unit specific marker to the target polymer, nor should it impact upon the binding specificity of the unit specific marker.

Other labels that may be used according to the invention include but are not limited to electron spin resonance molecule, a fluorescent molecule, a chemiluminescent molecule, a radioisotope, an enzyme substrate, an enzyme, a biotin molecule, an avidin molecule, an electrical charge transferring molecule, a semiconductor nanocrystal, a semiconductor nanoparticle, a colloid gold nanocrystal, a ligand, a microbead, a magnetic bead, a paramagnetic molecule, a quantum dot, a chromogenic substrate, an affinity molecule, a protein, a peptide, nucleic acid, a carbohydrate, a hapten, an antigen, an antibody, an antibody fragment, and a lipid.

Radioisotopes can be detected with film or charge coupled devices (CCDs), ligands can be detected by binding of a receptor having a fluorescent, chemiluminescent or enzyme tag, and microbeads can be detected using electron or atomic force microscopy. The label can be incorporated into the unit specific marker at the time of synthesis or by conjugation following synthesis.

A "detectable signal" as used herein is any type of signal which can be sensed by conventional technology. The signal produced depends on the type of energy source as well as the nature of the marker and its label. Preferably the signal is electromagnetic radiation resulting from light emission from the labeled unit specific marker bound to the polymer.

The labels bound to unit specific marker may be of the same type, e.g., they may all be fluorescent labels, or they may all be radioactive labels, or they may all be nuclear magnetic labels. This latter configuration may be preferable in some embodiments. Labels that are of the same type are still distinguishable from each other based on the signal they produce once in contact with an energy source (such as for example optical radiation). As an example, two fluorescent labels are distinguishable if they emit fluorescent radiation of different wavelengths. Alternatively, the unit specific marker labels may be of a different type, e.g., one label may be a fluorescent label and one may be a radioactive label.

A "light emissive compound" or "light emitting compound" as used herein is a compound that emits light in response to irradiation with light of a particular wavelength. These compounds are capable of absorbing and emitting light through phosphorescence, chemiluminescence, luminescence, polarized fluorescence, or, more preferably, fluorescence. The particular light emissive compound selected will depend on a variety of factors which are discussed in greater detail below.

Chemiluminescent compounds are compounds which luminesce due to a chemical reaction. Phosphorescent compounds are compounds which exhibit delayed luminescence as a result of the absorption of radiation. Luminescence is a non-thermal emission of electromagnetic radiation by a material upon excitation. These compounds are well known in the art.

Generally, fluorescent compounds are hydrocarbon molecules having a chain of several conjugated double bonds. The absorption and emission wavelengths of a dye are approximately proportional to the number of carbon atoms in the conjugated chain. A preferred fluorescent compound is "Cy-3" (Biological Detection Systems, Pittsburgh, Pa.). Other preferred fluorescent compounds useful according to the invention include but are not limited to fluorescein isothiocyanate ("FITC"), Texas Red™, tetramethylrhodamine isothiocyanate ("TRITC"), 4, 4-difluoro-4-bora-3a, and 4a-diaza-s-indacene ("BODIPY"), Cy-Chrome™, R-phycoerythrin (R-PE), PerCP, allophycocyanin (APC), PharRed™, Mauna Blue, Alexa™ 350, and Cascade Blue®. Some light emissive compounds are combinations of fluorophores. These compounds are often referred to as "piggyback" fluorophores because they are comprised of two fluorophores in close proximity to each other. In such compounds, one of the fluorophores is able to absorb the energy from the laser source, and emits energy when returning to the ground state which the other fluorophore can absorb. The resulting signal is derived from the second fluorophore upon its return to a less excited state. Piggyback compounds expand the fluorescent signals which can be derived from an energy source of a single wavelength.

In one embodiment of the invention the light emissive compound is a donor or an acceptor fluorophore. A fluorophore as used herein is a molecule capable of absorbing light at one wavelength and emitting light at another wavelength. A donor fluorophore is a fluorophore which is capable of transferring its fluorescent energy to an acceptor molecule in close proximity. An acceptor fluorophore is a fluorophore that can accept energy from a donor at close proximity. (An acceptor does not have to be a fluorophore. It may be non-fluorescent.) Fluorophores can be photochemically promoted to an excited state, or higher energy level, by irradiating them with light. Excitation wavelengths are generally in the ultraviolet, blue, or green regions of the spectrum. The fluorophores remain in the excited state for a very short period of time before releasing their energy and returning to the ground state. Those fluorophores that dissipate their energy as emitted light are donor fluorophores. The wavelength distribution of the outgoing photons forms the emission spectrum, which peaks at longer wavelengths (lower energies) than the excitation spectrum, but is equally characteristic for a particular fluorophore.

Table 1 indicates the various types of light emissive compounds available, along with their characteristic absorption and emission spectra and lasers that are suitable for their excitation. Fluorescently conjugated nucleotides, such as Cy3 and Cy5 labeled thymidine and cytosine, are commercially available from Amersham Pharmacia Biotech. Single labeled nucleotides are used in a standard automated nucleic acid synthesis along with non-labeled versions of the remaining three nucleotides. Depending upon the nucleotide content of the unit specific marker being synthesized (i.e., the nucleic acid probe), it may be necessary to include both labeled and unlabeled versions of the same nucleotide in a given synthesis reaction, in order to equalize the fluorescence from different unit specific markers.

Although most fluorophores exhibit a peak wavelength of emission, their emission spectra also span a range of wavelengths, resulting in the possibility that one fluorophore may emit into the detection channel of another fluorophore. In order to reduce the overlap in fluorescence between fluorophores, the signal from each into the detector of another is attenuated by compensation. This technique is known and routinely practiced in the art of flow cytometry. Briefly, a proportion of the signal from each fluorophore into its intended detector is subtracted from the signal the same fluorophore emits into the detector of another fluorophore. Compensation should be performed when using combinations of fluorophores having broad, overlapping emission spectra.

TABLE 1

| Compound | Absorption Wavelength (nm) | Emission Wavelength (nm) | Laser Type and Wavelength (nm) |
|---|---|---|---|
| Marina Blue | 360 | 460 | |
| Alexa ™ 350 | 360 | 445 | |
| Cascade Blue ® | 408 | 430 | 405 nm diode |
| Cascade Yellow | 408 | 510 | 405 nm diode |
| Flourescein (FITC) | 488 | 525 | 488 nm Argon |
| Phycoerythrin (R-PE) | 488 | 575 | 488 nm Argon |
| Cy-Chrome ™ (Cy-5) | 488 | 670 | 488 nm Argon |
| PerCP ™ | 488 | 675 | 488 nm Argon |
| Texas Red ® | 595 | 610 | Argon-Krypton or Dye |
| APC | 595 | 660 | Helium-Neon or Krypton |
| PharRed ™ (Cy7-APC) | 595 or 633 | 780 | Helium-Neon |
| BODIPY Rhodamine (TRITC) | 544 | 572 | 532 nm or 543 nm |

Radioactive compounds are substances which emit alpha, beta or gamma nuclear radiation. Alpha rays are positively charged particles of mass number 4 and slightly deflected by electrical and magnetic fields. Beta rays are negatively charged electrons and are strongly deflected by electrical and magnetic fields. Gamma rays are photons of electromagnetic radiation and are undeflected by electrical and magnetic fields and are of wavelength of the order of $10^{-8}$ to $10^{-9}$ cm. The radioactive compound emits nuclear radiation as it passes the station. When the station is a scintillation layer, the nuclear radiation interacts with the scintillation layer and causes fluorescent excitation. A fluorescent signal indicative of the radioactively labeled marker can then be detected.

The unit specific markers and/or polymers can be labeled using antibodies or antibody fragments and their corresponding antigen or hapten binding partners. Detection of such bound antibodies and proteins or peptides is accomplished by techniques well known to those skilled in the art. Use of hapten conjugates such as digoxigenin or dinitrophenyl is also well suited herein. Antibody/antigen complexes which form in response to hapten conjugates are easily detected by linking a label to the hapten or to antibodies which recognize the hapten and then observing the site of the label. Alternatively, the antibodies can be visualized using secondary antibodies or fragments thereof that are specific for the primary antibody used. Polyclonal and monoclonal antibodies may be used. Antibody fragments include Fab, F(ab)$_2$, Fd and antibody fragments which include a CDR3 region. The conjugates can also be labeled using dual specificity antibodies.

In still another embodiment, the polymer is labeled with a sequence independent label, including backbone labels. If the polymer is a nucleic acid, the sequence independent label is referred to as a nucleic acid stain. Nucleic acid stains can be intercalating dyes such as phenanthridines and acridines (e.g., ethidium bromide, propidium iodide, hexidium iodide, dihydroethidium, ethidium homodimer-1 and -2, ethidium monoazide, and ACMA); minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc. Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, Oli-Green, RiboGreen, SYBR Gold, SYBR Green 1, SYBR Green II, SYBR DX, SYTO-40,-41,-42,-43,-44,-45 (blue), SYTO-13,-16,-24,-21,-23,-12,-11,-20,-22,-15,-14,-25 (green), SYTO-81,-80,-82,-83,-84,-85 (orange), SYTO-64,-17,-59,-61,-62,-60,-63 (red).

The unit specific marker and the extrinsic label are conjugated or linked to each other. Extrinsic labels can be linked or conjugated to the unit specific marker by any means known in the art. For example, the labels may be attached directly to the unit specific marker or attached to a linker which is attached to the unit specific marker. Unit specific markers can be chemically derivatized to include linkers or to facilitate binding to linkers in order to enhance this process. For instance, fluorophores have been directly incorporated into nucleic acids by chemical means but have also been introduced into nucleic acids through active amino or thiol groups in on introduced into nucleic acids. (Proudnikov and Mirabekov, Nucleic Acid Research, 24:4535-4532, 1996.) An extensive description of modification procedures that can be performed on the marker, the linker and/or the label can be found in Hermanson, G.T., Bioconjugate Techniques, Academic Press, Inc., San Diego, 1996, which is hereby incorporated by reference.

There are several known methods of direct chemical labeling of DNA (Hermanson, 1996; Roget et al., 1989; Proudnikov and Mirabekov, 1996). One of the methods is based on the introduction of aldehyde groups by partial depurination of DNA. Fluorescent labels with an attached hydrazine group are efficiently coupled with the aldehyde groups and the hydrazine bonds are stabilized by reduction with sodium labeling efficiencies around 60%. The reaction of cytosine with bisulfite in the presence of an excess of an amine fluorophore leads to transamination at the N4 position (Hermanson, 1996). Reaction conditions such as pH, amine fluorophore concentration, and incubation time and temperature affect the yield of products formed. At high concentrations of the amine fluorophore (3M), transamination can approach 100% (Draper and Gold, 1980).

In addition to the above method, it is also possible to synthesize nucleic acids de novo (e.g., using automated nucleic acid synthesizers) using fluorescently labeled nucleotides. Such nucleotides are commercially available from suppliers such as Amersham Pharmacia Biotech, Molecular Probes, and New England Nuclear/Perkin Elmer.

Light emissive compounds can be attached to unit specific markers or by any mechanism known in the art. For instance, functional groups which are reactive with various light emissive groups include, but are not limited to, (functional group: reactive group of light emissive compound) activated ester: amines or anilines; acyl azide:amines or anilines; acyl halide: amines, anilines, alcohols or phenols; acyl nitrile:alcohols or phenols; aldehyde:amines or anilines; alkyl halide:amines, anilines, alcohols, phenols or thiols; alkyl sulfonate:thiols, alcohols or phenols; anhydride:alcohols, phenols, amines or anilines; aryl halide:thiols; aziridine:thiols or thioethers; carboxylic acid:amines, anilines, alcohols or alkyl halides; diazoalkane:carboxylic acids; epoxide:thiols; haloacetainmide: thiols; halotriazine:amines, anilines or phenols; hydrazine: aldehydes or ketones; hydroxyamine:aldehydes or ketones; imido ester:amines or anilines; isocyanate:amines or anilines; and isothiocyanate:amines or anilines.

The labeled polymer is exposed to an energy source in order to generate a signal from the label. As used herein, the labeled polymer is "exposed" to an energy source by positioning or presenting the labeled unit specific marker bound to the polymer in interactive proximity to the energy source such that energy transfer can occur from the energy source to the labeled unit specific marker, thereby producing a detectable signal. Interactive proximity means close enough to permit the interaction or change which yields that detectable signal.

The energy source may be selected from the group consisting of electromagnetic radiation, and a fluorescence excitation source, but is not so limited. "Electromagnetic radiation" as used herein is energy produced by electromagnetic waves. Electromagnetic radiation may be in the form of a direct light source or it may be emitted by a light emissive compound such as a donor fluorophore. "Light" as used herein includes electromagnetic energy of any wavelength including visible, infrared and ultraviolet. A fluorescence excitation source as used herein is any entity capable of making a source fluoresce or give rise to photonic emissions (i.e. electromagnetic radiation, directed electric field, temperature, physical contact, or mechanical disruption.)

In one aspect, the method further involves exposing the labeled polymer to a station to produce distinct signals arising from the labels of the unit specific markers. As used herein, a labeled polymer is "exposed" to a station by positioning or presenting the labeled unit specific marker bound to the polymer in interactive proximity to the station such that energy transfer or a physical change in the station can occur, thereby producing a detectable signal. A "station" as used herein is a region where a portion of the polymer (having a labeled unit specific marker bound thereto) is exposed to an energy source in order to produce a signal or polymer dependent impulse. The station may be composed of any material including a gas, but preferably the station is a non-liquid material. In one preferred embodiment, the station is a composed of a solid material. If the labeled unit specific marker interacts with the energy source at the station, then it is referred to as an interaction station. An "interaction station" is a region where a labeled unit specific marker and the energy source can be positioned in close enough proximity to each other to facilitate their interaction. The interaction station for fluorophores is that region where the labeled unit specific marker and the energy source are close enough to each other that they can energetically interact to produce a signal.

When the labeled unit specific markers are sequentially exposed to the station and/or the energy source, the marker (and thus polymer) and the station and/or the energy source move relative to each other. As used herein, when the marker and the station and/or energy source move relative to each other, this means that either the marker (and thus polymer) or the station and/or the energy source are both moving, or alternatively only one of the two is moving and other is stationary. Movement between the two can be accomplished by any means known in the art. As an example, the marker and polymer can be drawn past a stationary station by an electric current. Other methods for moving the marker and polymer past the station include but are not limited to magnetic fields, mechanical forces, flowing liquid medium, pressure systems, suction systems, gravitational forces, and molecular motors (e.g., DNA polymerases or helicases if the polymer is a nucleic acid, and myosin when the polymer is a peptide such as actin). Polymer movement can be facilitated by use of channels, grooves, or rings to guide the polymer. The station is constructed to sequentially receive the target polymer (with labeled unit specific markers bound thereto) and to allow the interaction of the label and the energy source.

The interaction station in a preferred embodiment is a region of a nanochannel where a localized energy source can interact with a polymer passing through the channel. The point where the polymer passes the localized region of agent is the interaction station. As each labeled unit specific marker passes by the energy source a detectable signal is generated. The energy source may be a light source which is positioned a distance from the channel but which is capable of transporting light directly to a region of the channel through a waveguide. An apparatus may also be used in which multiple polymers are transported through multiple channels. The movement of the polymer may be assisted by the use of a groove or ring to guide the polymer.

Other arrangements for creating interaction stations are embraced by the invention. For example, a polymer can be passed through a molecular motor tethered to the surface of a wall or embedded in a wall, thereby bringing units of the polymer sequentially to a specific location, preferably in interactive proximity to the energy source, thereby defining an interaction station. U.S. Pat. No. 6,210,896, to Eugene Chan, which is directed to Molecular Motors is hereby incorporated by reference in its entirety. A molecular motor is a compound such as polymerase or helicase which interacts with the polymer and is transported along the length of the polymer past each unit. Likewise, the polymer can be held stationary and a reader can be moved along the polymer, the reader having attached to it the energy source. For instance the energy source may be held within a scanning tip that is guided along the length of the polymer. Interaction stations then are created as the energy source is moved into interactive proximity to each labeled unit specific marker.

As discussed earlier many methods may be used to move the polymer linearly across the channel and past the interaction station or signal generation station. A preferred method according to the invention utilizes and electric field. An electric field can be used to pull a polymer through a channel because the polymer becomes stretched and aligned in the direction of the applied field as has previously been demonstrated in several studies (Bustamante, 1991; Gurrieri et al., 1990; Matsumoto et al., 1981). The most related experiments regarding linear crossing of polymers through channels arise from experiments in which polymeric molecules are pulled through protein channels with electric fields as described in Kasianowicz et al., 1996 and Bezrukov et al., 1994, each of which is hereby incorporated by reference.

In order to achieve optimal linear crossing of a polymer across a channel it is important to consider the channel diameter as well as the method used to direct the linear crossing of the polymer e.g., an electric field. The diameter of the channels should correspond well with that of the labeled polymer. The theory for linear crossing is that the diameter of the channels correspond well with that of the polymer. For example the ring-like sliding clamps of DNA polymerases have internal diameters that correspond well with the diameter of double-stranded DNA and are successful at achieving linear crossing of a DNA molecule. Many kilobases of DNA can be threaded through the sliding clamps. Several references also have demonstrated that linear crossing of DNA through channels occurs when the diameter of the channels corresponds well with that of the diameter of the DNA. (Bustamante, 1991; Gurrieri et al., 1990; Matsumoto et al., 1981).

Single-stranded DNA, as used in the experiment, has a diameter of ~1.6-nm. A channel having an internal diameter of approximately 1.7-3 nm is sufficient to allow linear crossing of a single strand DNA molecule. The diameters of the channel and the DNA need not match exactly but it is preferred that they be similar. For double-stranded DNA which has a diameter of 3.4-nm, channel sizes between 3.5-nm and 4.5-nm are sufficient to allow linear crossing.

The interaction station uses unique arrangements and geometries that allow the localized radiation spot to interact with one or several polymer units or unit specific marker labels that are on the order of nanometers or smaller. Optical detector detects light modified by the interaction and provides a detection signal to the processor.

As the labeled polymer passes through interaction station, the optical source emits radiation electric or electromagnetic field, X-ray radiation, or visible or infrared radiation for characterizing the polymer passing through the interaction station directed to an optical component of interaction station. The optical component produces a localized radiation spot that interacts directly with a) the polymer backbone (e.g., when the polymer backbone is bound to an intercalator that emits radiation), b) labels attached to the unit specific markers, or c) both the backbone units and the labels. The localized radiation spot includes non-radiating near field or an evanescent wave, localized in at least one dimension. The localized radiation spot provides a much higher resolution than the diffraction-limited resolution used in conventional optics.

The interaction between the labeled unit specific marker and the agent can take a variety of forms. As a first example, the interaction can take place between an energy source that is electromagnetic radiation and a labeled unit specific marker that is a light emissive compound (preferably, a unit specific marker that is extrinsically labeled with a light emissive compound). When the light emissive compound is exposed to the electromagnetic radiation (such as by a laser beam of a suitable wavelength or electromagnetic radiation emitted from a donor fluorophore), the electromagnetic radiation causes the light emissive compound to emit electromagnetic radiation of a specific wavelength. A second type of interaction involves an energy source that is a fluorescence excitation source and a unit specific marker that is labeled with a light emissive compound. When the light emissive unit is contacted with the fluorescence excitation source, the fluorescence excitation source causes the light emissive compound to emit electromagnetic radiation of a specific wavelength. In both examples, the signal that is measured exhibits a characteristic pattern of light emission, indicating that a particular unit of the polymer is present at that particular location.

A variation of these types of interaction involves the presence of a third element of the interaction, a proximate compound which is involved in generating the signal. For example, a unit specific marker may be labeled with a light emissive compound which is a donor fluorophore and a proximate compound can be an acceptor fluorophore. If the light emissive compound is placed in an excited state and brought proximate to the acceptor fluorophore, then energy transfer will occur between the donor and acceptor, generating a signal which can be detected as a measure of the presence of the unit specific marker which is light emissive. The light emissive compound can be placed in the "excited" state by exposing it to light (such as a laser beam) or by exposing it to a fluorescence excitation source.

A set of interactions parallel to those described above can be created in which the light emissive compound is the proximate compound and the labeled unit specific marker is an acceptor source. In these instances the energy source is electromagnetic radiation emitted by the proximate compound, and the signal is generated by bringing the labeled unit specific marker in interactive proximity with the proximate compound.

The mechanisms by which each of these interactions produce detectable signals are known in the art. PCT applications WO98/35012 and WO00/09757, published on Aug. 13, 1998 and Feb. 24, 2000 respectively, and U.S. Pat. No. 6,355,420 B1 issued Mar. 12, 2002, describe the mechanism by which a donor and acceptor fluorophore interact according to the invention to produce a detectable signal including practical limitations which are known to result from this type of interaction and methods of reducing or eliminating such limitations.

In some embodiments, the system also provides for polymer alignment. The fabrication of the alignment region, the microchannel and the slits has been described before in Published PCT Application No. WO 00/09757.

According to the methods described herein, each analysis intends to capture or detect preferably two or more detectable signals. As described herein, a first unit specific marker can interact with the energy source to produce a first signal and a second unit specific marker can interact with the energy source to produce a second signal. The signals so produced are different and thus distinct from one another. Distinct signals as used herein refer to signals which can be differentiated from one another. This enables more than one type of unit to be detected on a single target polymer. This also enables units more thorough sequencing of a target polymer since units located at distances smaller than the resolution limit of prior art approaches can now to detected separately and their positions can be distinguished and thus mapped along the length of the polymer.

Once the signal is generated it can then be detected. The particular type of detection means will depend on the type of signal generated which of course will depend on the type of interaction which occurs between the unit and the energy source. Most of the interactions involved in the method will produce an electromagnetic radiation signal. Many methods are known in the art for detecting electromagnetic radiation signals. Preferred devices for detecting signals are two-dimensional imaging systems that have, among other parameters, low noise, high quantum efficiency, proper pixel-to-image correlation, and efficient processing times. An example of a device useful for detecting signals is a two-dimensional fluorescence imaging system which detects electromagnetic radiation in the fluorescent wavelength range.

The detectable signals can be distinguished from each other by using multiple detectors each of which detects signals of a specific wavelength or of a narrow range of wavelengths. In addition, signals can be resolved using various dichroic reflectors, mirrors and/or band pass filters in the optical path to separate different emission wavelengths, each of which is characteristic of a particular label (and thus a particular unit specific marker). The configuration of detectors will govern the requirement and placement of such mirrors and filters. Mirrors can be used to deflect signals below a particular wavelengths towards low wavelength detectors. Filters can be used to remove excitation wavelengths that are merely scattered by the polymer. Bandpass filters allow wavelengths of a particular range to pass through, and block all other wavelengths. Longpass filters allow wavelengths above a particular set minimum to pass. It is within the skill of the ordinary artisan to determine the placement of optical mirrors and filters along the length of the fluorescent beam radiating from the labeled unit specific markers.

The detectable signals so generated are captured by and preferably recorded by a detection device, optionally at or within a detection station. As stated earlier, the detectable signal produced by each labeled unit specific marker is indicative of that particular marker, its sequence and corresponding the complementary unit in the target polymer to which the marker is bound. Signals are detected sequentially when signals from different markers are detected spaced apart in time (and thus distance along the length of the target polymer). Not all units need to be detected or need to generate a signal to detect signals "sequentially". The temporal separation of the peak outputs from the detection channels, together with knowledge of the velocity at which the polymer is moving past the station (or the velocity at which the station is moving past the polymer) is used to calculate the distance between the two marker positions.

The invention is not limited in scope to the type of detection technology used. Rather, the method described herein may be adapted to any system capable of detecting sequence-specific tags on a linear polymer such as DNA. There are a number of detection schemes that would lend themselves to this type of analysis, including optical and non-optical approaches. These detection systems include, but are not limited to, electron spin resonance detection, atomic force microscope (AFM) detection, scanning tunneling microscope (STM) detection, optical detection, nuclear magnetic resonance (NMR) detection, near-field detection, fluorescence resonance energy transfer (FRET) detection, an electrical detection system, a photographic film detection system, a chemiluminescent detection system, an enzyme detection system, and an electromagnetic detection system. As an example of a suitable detection scheme, a scanning tunneling system could be used to analyze sequence information from linear polymers provided that unit specific markers are labeled with compounds that are distinguishable using the scanning tunneling system. Similarly, the detection technologies described in PCT published patent applications WO98/35012 and WO00/09757, published on Aug. 13, 1998 and Feb. 24, 2000, respectively and in issued U.S. Pat. No. 6,355,420 B1, issued Mar. 12, 2002, can be used in conjunction with their respective labeling technologies for high-resolution linear analysis in accordance with the methods of the invention. The entire contents of these patent applications are incorporated by reference herein in their entirety.

The signals detected following the interaction of the energy source and the labeled specific marker may be stored in a database for analysis. One method of analyzing the stored signals is to align them in order to derive sequential linear sequence information about the polymer. By running two or more analyses, all of which contain as a control the same labeled unit specific marker, it is possible to combine the sequence information from the analyses, thereby yielding even more information than would possibly be achieved in a single analysis. Another method for analyzing the stored signals is to compare the stored signals to a pattern of signals from another polymer to determine the relatedness of the two polymers. Yet another method for analyzing of the detected signals is to compare the detected signals to a known pattern of signals characteristic of a known polymer to determine the relatedness of the polymer being analyzed to the known polymer. Comparison of signals is discussed in more detail below.

In one aspect, the methods of the invention can be used to identify one, some, or all of the units of the polymer. This is achieved by identifying the type of individual unit and its position on the backbone of the polymer by determining whether a signal detected at that particular position on the backbone is characteristic of the presence of a particular labeled unit.

The methods of the invention also are useful for identifying other structural properties of polymers. The structural information obtained by analyzing a polymer according to the methods of the invention may include the identification of characteristic properties of the polymer which (in turn) allows, for example, for the identification of the presence of a polymer in a sample or a determination of the relatedness of polymers, identification of the size of the polymer, identification of the proximity or distance between two or more individual units of a polymer, identification of the order of two or more individual units within a polymer, and/or identification of the general composition of the units of the polymer. Such characteristics are useful for a variety of purposes such as determining the presence or absence of a particular polymer in a sample. For instance when the polymer is a nucleic acid the methods of the invention may be used to determine whether a particular genetic sequence is expressed in a cell or tissue.

The presence or absence of a particular sequence can be established by determining whether any polymers within the sample express a characteristic pattern of individual units which is only found in the polymer of interest i.e., by comparing the detected signals to a known pattern of signals characteristic of a known polymer to deterimine the relatedness of the polymer being analyzed to the known polymer. The entire sequence of the polymer of interest does not need to be determined in order to establish the presence or absence of the polymer in the sample. Similarly the methods may be useful for comparing the signals detected from one polymer to a pattern of signals from another polymer to determine the relatedness of the two polymers.

Once all of the detectable signals are generated, detected and stored in a database the signals can be analyzed to determine structural information about the polymer. The computer may be the same computer used to collect data about the polymers, or may be a separate computer dedicated to data analysis. A suitable computer system to implement the present invention typically includes an output device which displays information to a user, a main unit connected to the output device and an input device which receives input from a user. The main unit generally includes a processor connected to a memory system via an interconnection mechanism. The input device and output device also are connected to the processor and memory system via the interconnection mechanism.

It should be understood that one or more output devices may be connected to the computer system. Example output devices include a cathode ray tube (CRT) display, liquid crystal displays (LCD), printers, communication devices such as a modem, and audio output. It should also be understood that one or more input devices may be connected to the computer system. Example input devices include a keyboard, keypad, track ball, mouse, pen and tablet, communication device, and data input devices such as sensors. It should be understood the invention is not limited to the particular input or output devices used in combination with the computer system or to those described herein.

The computer system may be a general purpose computer system which is programmable using a high level computer programming language, such as C or C++. The computer system may also be specially programmed, special purpose hardware. In a general purpose computer system, the processor is typically a commercially available processor, of which the series x86 processors, available from Intel, and similar devices from AMD and Cyrix, the 680X0 series microprocessors available from Motorola, the PowerPC microprocessor from IBM and the Alpha-series processors from Digital Equipment Corporation, are examples. Many other processors are available. Such a microprocessor executes a program called an operating system, of which WindowsNT, UNIX, DOS, VMS and OS8 are examples, which controls the execution of other computer programs and provides scheduling, debugging, input/output control, accounting, compilation, storage assignment, data management and memory management, and communication control and related services. The processor and operating system define a computer platform for which application programs in high-level programming languages are written.

A memory system typically includes a computer readable and writeable nonvolatile recording medium, of which a magnetic disk, a flash memory and tape are examples. The disk may be removable, known as a floppy disk, or permanent, known as a hard drive. A disk has a number of tracks in which signals are stored, typically in binary form, i.e., a form interpreted as a sequence of one and zeros. Such signals may define an application program to be executed by the microprocessor, or information stored on the disk to be processed by the application program. Typically, in operation, the processor causes data to be read from the nonvolatile recording medium into an integrated circuit memory element, which is typically a volatile, random access memory such as a dynamic random access memory (DRAM) or static memory (SRAM). The integrated circuit memory element allows for faster access to the information by the processor than does the disk. The processor generally manipulates the data within the integrated circuit memory and then copies the data to the disk when processing is completed. A variety of mechanisms are known for managing data movement between the disk and the integrated circuit memory element, and the invention is not limited thereto. It should also be understood that the invention is not limited to a particular memory system.

It should be understood the invention is not limited to a particular computer platform, particular processor, or particular high-level programming language. Additionally, the computer system may be a multiprocessor computer system or may include multiple computers connected over a computer network.

The data stored about the polymers may be stored in a database, or in a data file, in the memory system of the computer. The data for each polymer may be stored in the memory system so that it is accessible by the processor independently of the data for other polymers, for example by assigning a unique identifier to each polymer.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Different Fluorescent Sequence-specific Tags

There are many different types of fluorescent sequence-specific tags. These include fluorescent tags that can be differentiated by their emission spectra. Examples of fluorescent tags include standard dyes such as fluorescein, Cy3 and Cy5, all of which have different fluorescence emission spectra that can be distinguished using standard spectral filtering techniques. These techniques include dichroic mirrors, bandpass filters, notch filters, and combinations thereof. Fluorescent tags having the same spectra can also be distinguished by means of fluorescence lifetime determination. Fluorescence lifetime is the time between excitation and emission of a photon of a given fluorophore. For standard fluorophores such as those described, the fluorescence lifetime is on the order of 1 nanosecond to 5 nanoseconds. The use of two fluorophores with the same emission spectra but different lifetimes is another approach to multiplex the number of sequence-specific tags in the system.

Example 2

Different Scanning Tunneling Sequence-specific Tags

The use of non-fluorescent based approaches for differential tagging and high-resolution linear analysis may include the use of scanning tunneling tips for the analysis and scanning of linear molecules such as DNA at high speeds. Using this technique, sequence specific tags may include gold particles, silica particles, as well as nanocrystals. Since scanning tunneling tips are capable of size discrimination, differential tagging approaches can exploit different sized particles as probe labels.

Example 3

Different Types of Fluorophores Suitable for use with Monochromatic Excitation and Multicolor Detection Systems There are a number of different types of fluorophores that can be used in systems comprising monochromatic excitation (e.g., single laser systems) and multicolor detectors. For example, for fluorescence-based approaches, the tags that can be spectrally distinguished based on their differential emission spectra include dyes such as Cascade Blue, Alexa dyes, Cy dyes, tetramethylrhodamine (TAMRA), rhodamine-6G, infrared dyes, Texas Red™, Oregon Green, fluorescein, all of which are commercially available from a number of sources including but not limited to Molecular Probes, OR.

As stated in Example 2, size can also be used to differentiate tags. Scanning tunneling based approaches can use semiconductor nanocrystals which yield size-dependent spectra. For instance, a 4 nm CdSe nanocrystal yields a different spectral emission than a 3 nm CdSe nanocrystal. Silica, gold, latex and ferritin particles can also be used in size discrimination systems. Different tags may have different properties included electrical, magnetic, chemical, and biological properties.

Example 4

Experimental Apparati for Fluorescence Detection

Various experimental apparati can be used in conjunction with the methods of the invention in order to obtain sequence information from linear polymers such as DNA molecules. Several experimental apparati are described in PCT published patent applications WO98/35012 and WO00/09757, and in U.S. Pat. No. 6,355,420 B1. These approaches are used to elongate DNA, deliver it to multiple excitation regions, and detect fluorescence from various excitation regions along the length of the DNA. Other approaches that are suitable employ a molecular motor to read a strand of DNA, yet still detect fluorescence along the length of the DNA using a detection system. These latter methods may employ a polymerase or other enzyme or protein capable of scanning DNA as the molecular molecule.

Physical detection systems may include CCD-based methods of imaging detection, confocal detection, electrical detection, multi-color methods of detection, near-field analysis, and FRET analysis. Other detection systems include single-color illumination methods such as confocal systems using a single laser excitation wavelength. The single color wavelength excites two different fluorescent entities which each have different emission wavelengths. A single-color illumination system may be preferable in some instances, particularly since it avoids the chromatic aberrations and parfocality problems that sometimes exist in dual excitation systems. These problems can also be overcome directly in dual excitation systems by using pre-aligned multiple wavelengths, such as is possible with multi-line argon-krypton laser systems. Fiber optic coupling of multiple laser lines can also achieve the same purpose. Cdnfocal detection systems using these latter laser arrangements are suitable for use in the methods of the invention.

Example 5

Sequence Interrogation Using Multi-Color Enhanced Resolution

Multi-color enhanced resolution methods can be applied to methods and probe sets used to obtain sequence information from a polymer such as DNA. Depending on how particular sequences of probes are labeled, different information can be obtained from the strand of DNA molecule. In the following Examples directed at DNA sequence analysis, a nucleic acid probe is used as the sequence-specific agent. Binding of the probe to the target DNA (i.e., the DNA intended to be analyzed) positions a fluorophore or a fluorochrome along the length of the DNA. The methods of the invention employ any number of means or methods for introducing, attaching or binding a fluorochrome or fluorophore (difference) to a probe. Methods of fluorophore incorporation into or conjugation to a nucleic acid probe are known to those of ordinary skill in the art. Accordingly, the method is not dependent upon the method of probe labeling provided that such labeling does not differentially compromise the binding capability of the probe to the target molecule.

Figure 2:
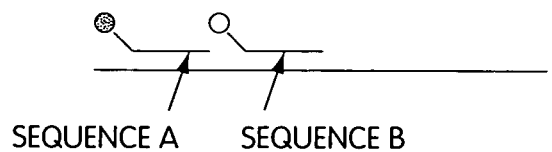
FIG. 2 is a schematic representation illustrating the binding of unit specific markers having specificity for different target sequences (i.e., units) on the target polymer being analyzed. The unit specific markers are conjugated with different labels (e.g., the unit specific marker with binding specificity for target sequence A is labeled with a red fluorescent molecule and the unit specific marker with binding specificity for target sequence B is labeled with a green fluorescent molecule).

In the simplest scenario, interrogation of a target sequence using two probes can be performed using differentially labeled probes directed at different target sequences. An example of this is shown in FIG. 2. In FIG. 2, a strand of DNA is bound at two adjacent sites with two probes having different labels and specificity for different target sequences. The two adjacent sites are located relative to each other in the sub-resolution of the detection zone of interest. In a confocal system, the sub-resolution of the detection zone of interest is below the $\lambda/2$ diffraction limit of the confocal spot. If the light wavelength is 532 nm, then this limit is 266 nm or 782 base-pairs of information.

In some embodiments of the invention, and depending on the detection system used and the number of markers used, it is possible to detect markers (and thus, units) separated from each other by less than 750 bp, less than 700 bp, less than 650 bp, less than 600 bp, less than 550 bp, less than 500 bp, less than 450 bp, less than 400 bp, less than 350 bp, less than 300 bp, less than 250 bp, less than 200 bp, less than 150 bp, less than 100 bp, or less than 50 bp.

Figure 3:
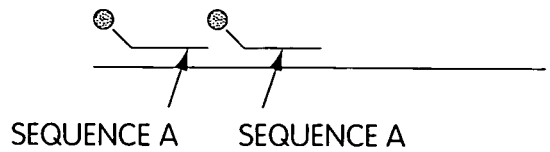
FIG. 3 is a schematic representation illustrating the binding of unit specific markers specific for identical target sequences (i.e., units) on the target polymer being analyzed. The unit specific markers are conjugated with identical labels (e.g., both unit specific markers have binding specificity for target sequence A and both are labeled with a green fluorescent molecule).

A second scenario involves using probes that have the same sequence (and thus the same target sequence specificity). FIG. 3 illustrates this situation. The distance between the two target sites would normally be below the resolution limit of the optical system as used in the prior art. If the target molecule is exposed to a solution of probes that share an identical fluorescent tag, then these probes will bind to adjacent target sequences on the target molecule and because of their identical labels will be incapable of resolution.

If however, the mixture of probes contains equal numbers of probes that are labeled with two different labels, then this spatial limitation is overcome. For instance, if 50% of the probe (or fluorescently tagged site) is labeled with red fluorophore (Cy5) and 50% of the probe is labeled with a green fluorophore (fluorescein), then because of the equimolar mixture of the differently labeled probes, there is a 50% probability that there will be one probe of either red or green attached to any one particular site. This results in $2^2$ (i.e., 4) possible combinations of how such probes would bind to two adjacent sites. These possible combinations of two distinctly labeled probes binding to two adjacent sites are illustrated in FIG. 4.

Figure 4:
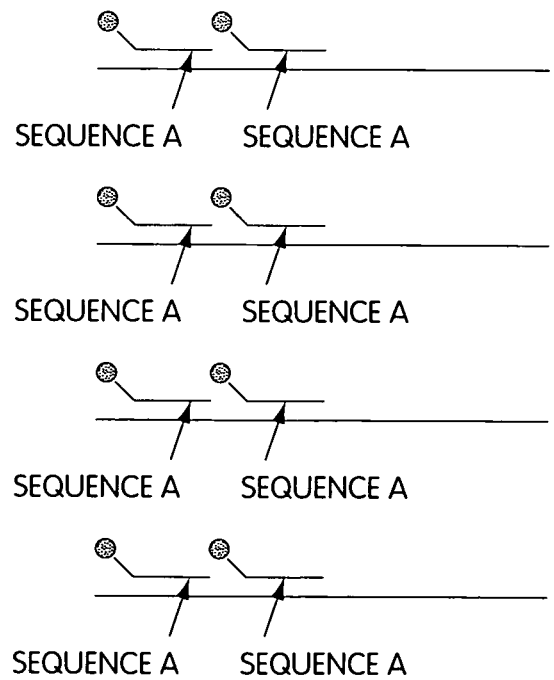
FIG. 4 is a schematic representation illustrating the binding of a mixture of identical unit specific markers having identical binding specificity to target polymers having two adjacent target sequences. In this case, 50% of the unit specific markers in the mixture are labeled with a green fluorescent molecule, and the remaining 50% are labeled with a red fluorescent molecule. Assuming that the particular label has no effect on the binding specificity of the unit specific marker, each unit specific marker can bind to both target sequences with equal probability. Accordingly, 25% of target polymers will have bound to them two unit specific markers both labeled with a green fluorescent molecule, and 25% of target polymers will have bound to them two unit specific markers both labeled with a red fluorescent marker. Target polymers that are bound in this way do not provide useful information in and of themselves because identical signals are not resolvable at distances within the spatial resolution. Information can however be derived from the remaining 50% of target polymers which have bound to them unit specific markers that are differentially labeled. In half of these latter cases, the target polymer has bound to it sequentially a green fluorescent unit specific marker and a red fluorescent unit specific marker. In the remaining half of cases (i.e., 25% of the total target polymers), the target polymer has bound to it sequentially a red fluorescent unit specific marker and a green fluorescent unit specific marker. Differentially labeled unit specific marker can be resolved from each other even if they are located closer than the spatial resolution of the system.

As illustrated in FIG. 4, half of the possible combinations, i.e., those in which both sites are bound by green labeled probes or both sites are bound by red labeled probes, will not be resolved. The bottom two combinations illustrated in FIG. 4 will be resolved however. In these combinations, the probes binding to adjacent sites are differently labeled, and provide either a green-red or a red-green pattern. Because of the ability to resolve the position of probes in this latter situation, useful sequence information from the DNA molecules can be achieved an high throughput linear analysis is possible.

Figure 5:
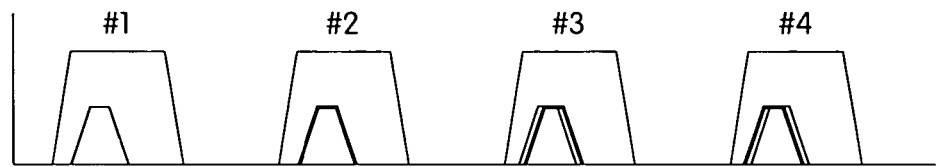
FIG. 5 is a schematic representation of the signal outputs from the target polymers labeled as in FIG. 4. The diagram also indicates the blue signal achieved from a blue fluorescent intercalator that binds to the nucleic acid polymer backbone. As indicated in FIG. 4, target polymers 1 and 2 emit a single indistinguishable (i.e., non-resolvable) signal. Target polymers 3 and 4 on the other hand emit slightly overlapping signals which can be resolved using the methods of the invention. The ability to resolve the location of the unit specific markers (and corresponding units) for target polymers 3 and 4 allows more sequence information to be retrieved, especially for unit specific markers (and corresponding units) that are located within the spatial resolution limit of prior art methods.

FIG. 5 illustrates the signals that can be achieved from the DNA molecules of FIG. 4 with the additional feature of a backbone stained with a blue intercalating compound. Signals 1 and 2 correspond to the top two probe placements in FIG. 4. Signal 3 and 4 correspond to the bottom two probe placements in FIG. 4. Signals 3 and 4 allow for dual-color increased resolution of adjacent tags, and thus only these probe arrangements are useful per se in deriving sequence information. If the identical sequence probes are labeled with the same label, then the probes cannot be distinguished from each other if the distance between them is less than the spatial resolution limit. If however identical sequence probes labeled with different labels are used the adjacent sites can be discerned from each other even if the distance between the sites (and thus the bound probes) is less than the spatial resolution limit.

The resolution offered by differential tagging is much greater than that offered by conventional tagging approaches using only one type of tag. Lacoste et al. (Lacoste, T.D. et al., Proc. Nat'l. Acad. Sci. 97(17):9461-9466.) give insight into the order of magnitude of the resolution that can be attained using a fluorescence-based detection system. In this study, Lacoste et al., report high-resolution interdistance determination between fluorescent species excited with a single excitation wavelength and with emissions at two different wavelengths. For instance, fluorescent transfluorospheres (TFS) and semiconductor nanocrystals (NC) were illuminated with a single laser line and particles emitting at two different spectral ranges could be distinguished when situated at least 25 nm apart. The general range of resolution was from 25 nm to 75 nm for the two-color imaging approach of LaCoste et al. The current invention takes this work several stages further in proposing a general high-resolution analysis method of linear DNA, either fixed or moving in a flow-based system. The second major part of the current invention is that various combinations of tagging strategies can allow the use of a differential tagging approach to interrogate information on DNA in a high-resolution rapid manner.

This minimal spatially resolvable distance corresponds approximately to 70 base-pairs of information. Thus, the method of the invention can be used to determine sequence information at 70 base pair intervals. This is a vast improvement over the current limit of 782 base pair intervals. Resolution of probes within 70 base pairs of each other approximates the distance between 3-mer probes (i.e., 64 base pairs between randomly placed probes of 3 nucleotides in length). The resolution that can be achieved using the methods of the present invention also enables the use of 4-mer probes which are randomly located within 256 base pairs of each other. This level of resolution could not be attained using the single color analysis methods of the prior art.

In the example of FIG. 4, each of the probe combinations has a 25% probability of occurring. Only one half of these combinations however will yield a valuable result. This probability is approximate however, since there will be instances in which only one of the adjacent sites is bound to a probe, and the other is free (or unlabeled), or in which only one site is detected by the system. Binding of probes can be maximized by increasing the ratio of probe to target molecule so that the amount of probe is not limiting. Moreover, binding efficiency can be increased by maximizing hybridization conditions corresponding to a given probe sequence.

The invention contemplates other approaches to increasing the efficiency of probe detection. For instance, the complexity of the probe mixture and the number of colors present in the probe mixture can be increased. As an example, a mixture of three differently labeled yet identical sequence probes can be used rather than the two label combination described above. If the mixture contains equal numbers of, for example, green labeled probes, red labeled probes and blue labeled probes, then each probe has a 33% chance of binding to either of the adjacent sites, assuming that binding at each site is independent of binding at the other. It follows then that binding of two adjacent sites by three different probes would result in 32 possible combinations of colors occupying the two sites. Three of these combinations will be unresolved combinations of colors because the same colored probe will bind to both sites. However, approximately 67% of the possible combinations will yield usable information. This is an increase over the 50% of usable combinations that could be achieved using only a two color probe mixture. A mixture of four differently labeled yet identical sequence probes similarly will yield 75% usable possible combinations. If the probe mixture contains 100 differently labeled probes, then 99% of the possible combinations yield useful information. Accordingly, the invention intends to embrace probe mixtures having 2, 3, 4, 5, 6, 7, 8, 9, 10, 20, 25, 30, 50, 75, 100 or more differently labeled probes.

As discussed above, the invention contemplates the use of probes of varying lengths including 3-mers, 4-mers, 5-mers, 6-mers, etc. If a 6-mer sequence recognition tags is used, and if nucleotides are randomly distributed throughout the genome, then any given 6-mer sequence would be predicted to occur every $4^6$ or 4096 base-pairs. Since the genome is not random, it is expected that there will be a range of distances between target sequences on the target DNA (and accordingly, a range of distances between bound probes on such a target DNA). This range might span from a few base-pairs to more than ten-thousand base-pairs. The greater resolution provided by the differential tagging system described herein allows resolution of 6-mer sequences that might occur within 4096 base pairs of each other. The high resolution method of the invention would not sacrifice the speed of passage of DNA molecules through the channel systems, particularly when probes are located within a short distance of each other. In fact, as stated above, probes located as close as 70 base pairs from each other should be resolvable using the methods described herein.

For instance, if the lambda genome is analyzed using the sequence specific tag GAATTC (6 base-pairs), then target sites will be separated from each other in the lambda genome by 3530, 4878, 5643, 5804, 7421 and 21226 base-pairs (including the end-tags of the lambda DNA). In this one example, there is a wide range of distances that may separate 6-mer probes or tags. Using a 6-mer probe having the sequence of AAGCTT, target sites will be separated from each other in the lambda genome by 2027, 2322, 4361, 6557, 9416 and 23130 base-pairs (including the end-tags of the lambda DNA). An optical system that was at a spatial resolution of 3000 base-pairs resolution prior to the discovery of the invention would be aided by the use of multi-color high resolution analysis and differential labeling of the same sites with different color tags. One of the advantages of this method of labeling is its ability to reduce the amount of DNA lost during throughput through the system.

The ability to multiplex different sequences using the differential tagging method of the invention different colors is diminished relative to monochromatic methods of labeling. In addition, a greater number of fragments of a given sequence need to be sampled using the differential tagging method in order to attain identical results as the monochromatic method. In an important embodiment, more than one color is assigned to a particular sequence. For example, if the high resolution method described herein employs four different colors, two of more of these colors will be assigned to a particular sequence. In so doing, the number of different sequences that can be analyzed at a given time is reduced. In the monochromatic method, each sequence can be assigned to a different color and accordingly, a greater number of sequences can be analyzed at the same time. The drawback of the monochromatic method is that contiguous target sequences that are situated within the resolution detection limit of the system are not detected. Using the high resolution method of the invention, fewer sequences can be analyzed at a given time, and more sample runs will be required, however, greater spatial resolution can be achieved. Accordingly, there is a trade-off between being able to analyze at higher spatial resolution and diminished multiplex capability, and a higher sampling requirement. Throughput estimates of the efficiency of differential tagging have been derived, and are presented below.

Assuming a monochromatic system that has a raw DNA delivery throughput of 10 million base-pairs per second (MB/s), a calculation for the amount of time to analyze one human genome at 10-fold coverage (i.e., analysis of 10 copies of the human genome) takes into consideration the following parameters:

| Parameter | Value |
| --- | --- |
| number of base-pairs in human genome | $2 * (3 \times 10^9) = 6 \times 10^9$ bp |
| % time actually collecting data from DNA | 20% |
| number of copies of human genome analyzed | 10x |

The total time to analyze a genome using 10 MB/s data rate is calculated as follows:
(number of base-pairs in human genome)
×(number of copies of human genome analyzed)
÷(throughput rate)
÷(% of time actually spent collecting data from DNA)
÷60÷60

Taking into consideration the values provided for this system, it would take 8.33 hours in a single detector collection system (i.e., a monochromatic system) to collect the information from a human genome sample, with 10-fold coverage. In a situation in which one six-iner is used, the amount of nucleic acid that can be sequenced in a single run is 6/4096 ×(the length of the molecule or genome).

Figure 6:
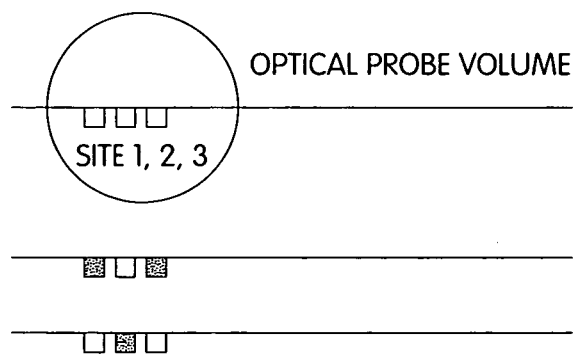
FIG. 6 is a schematic representation of the binding of differentially labeled unit specific markers along a polymer having three adjacent target sequences (i.e., units). The Figure shows the optimal binding pattern of unit specific markers to be one in which adjacent unit specific markers are conjugated to different fluorescent labels. In the situation in which the polymer has three adjacent units and half of the identical unit specific markers are labeled with a green fluorescent molecule and the remaining half are labeled with a red fluorescent molecule, there will be eight possible binding patterns, only two of which (i.e., 25%) will yield resolvable sequence information. The two most useful binding patterns are illustrated in the Figure.

Suppose instead that the system uses at least two differentially labeled probes. There is a finite probability that there are more than two target 6-mer sites within the optical resolution limit of the system. In order to determine the number of probes in the optical detection volume, it is necessary to determine the probability at which these probes are present in their alternating color schemes. An example of a situation in which there are three adjacent target sites and a mixture of three differently labeled (but identical sequence probes) is shown in FIG. 6. In order to determine that there are three sites within the optical probe volume by probability, the three sites must be occupied by alternating colored probes. In the case in which there are only two differently labeled probes, this happens 2 out of $2^3$ (i.e., 2 out of 8) times, or in 25% of the target DNA molecules.

The binding and detection efficiency will also affect the time required to perform the analysis. Assuming that this combined binding and detection efficiency is 90%, then there will be a 53% probability that all three sites will be occupied. This means that 12.5% of target molecules will be bound by the correct pattern of differently labeled probes required to determine if there are three target sites (and thus three bound probes) in the volume. It follows that a 10-fold coverage (i.e., analysis of 10 target molecules for each genome sample) is minimally sufficient to capture these less frequent events. In order to achieve statistically significant data, it might be necessary to analyze more than 10 copies per genome sample, and this in turn would lead to longer analysis times per genoine.

The enhanced resolution that can be achieved through differential tagging can be compared to that achievable using other methods of enhanced resolution, such as near-field analysis of the DNA. An examination of the real properties of a fluorophore in transit through a confocal illumination region demonstrates that a single fluorophore (in this one example) emits between 15-20 counts per bin. The DNA is travelling at 10,000 μm/sec with an approximate confocal spot size of 1 μm. The sampling rate is at 10 kHz. Therefore, each fluorophore spends 1 binwidth or 10 μs in the confocal laser spot. By decreasing the spot size, we decrease the captured signal proportionally. For instance, suppose that we decrease the illumination region to 200 nm using near-field analysis. This is 20% the illumination region. The pass-through rate of DNA would have to be reduced five-fold to ensure that the fluorescent probes are captured by the system. Alternatively, the sampling rate can be increased to 50 kHz to ensure that the passage of the individual fluorophores through the system is captured. A five-fold increase in the sampling rate leads to a decreased signal capture rate of 3-4 counts per bin. Trade-offs in using a smaller excitation volume include a decreased signal-to-noise ratio and/or a decreased throughput rate.

Figure 7:
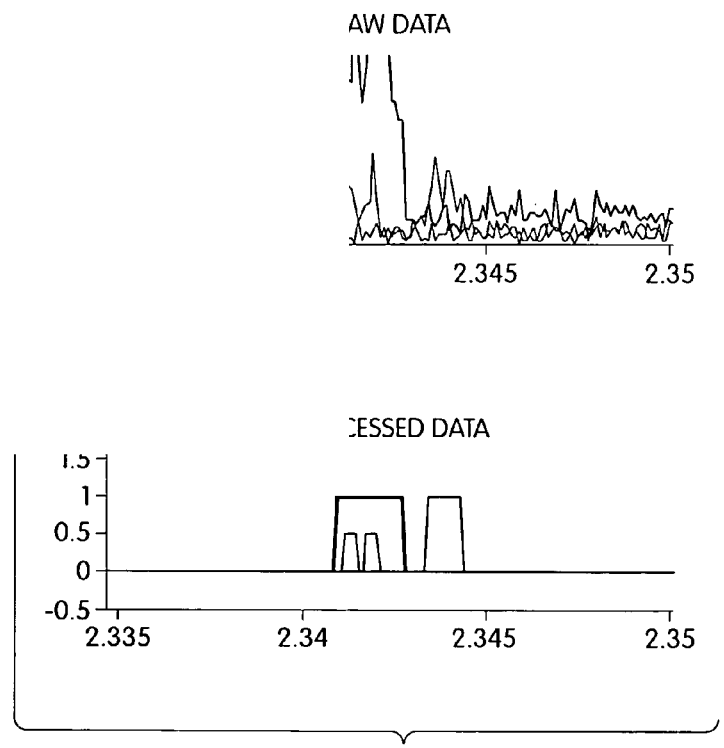
FIG. 7 is a schematic representation of data resulting from the passage of lambda DNA bound at two units. The lambda DNA passes through two detection regions. The first detection region captures the backbone and probe information from the DNA. The second detection region captures the backbone information at a fixed distance from the first detection region.

In contrast, the differential tagging method of the invention involves a different set of trade-offs. The signal-to-noise ratio and also potentially the throughput passage rate of the DNA molecules are not reduced. Instead, it is estimated that a larger number of molecules should be analyzed to give the same statistically significant positional information from the probes. The analysis is carried out in the previous example where to obtain identical statistics on the population set, the sample would need to be analyzed at a 10× greater redundancy. In small sample sizes, such as the analysis of small genomes up to several tens of MB (million base-pairs), this approach would be feasible for higher resolution. This approach may also be feasible for much larger genomes, if the trade-off in lesser statistics is immaterial. FIG. 7 illustrates the signals detected by running a lambda molecule through the system. The lambda molecule is labeled at two sites, and there are two detection regions (one for the backbone label and one for the probe).

Example 6

Scanning-Based Methods for High-Resolution Determination of Sequences

Figure 8:
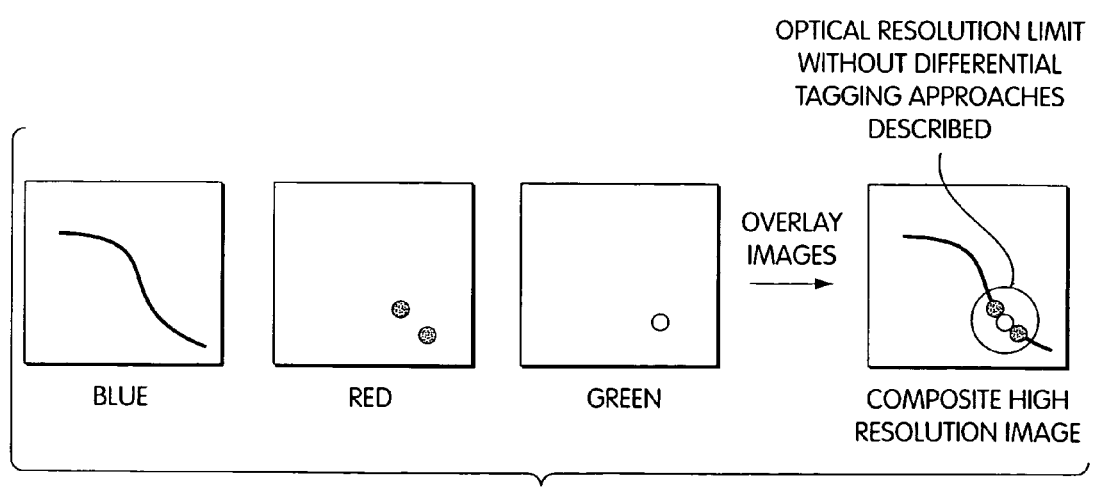
FIG. 8 is a schematic representation of detection patterns from a polymer (e.g., a nucleic acid) that has bound to it two red-labeled unit specific markers, one green-labeled unit specific marker and a blue intercalator along the backbone of the polymer. The Figure presents the individual images or spatially defined signals that can be achieved using three different detector systems. The Figure further illustrates the ability to overlay these individual images in order to arrive at a composite image showing the positioning of both labels along the length of the polymer.

The above described methods of tagging DNA using differential labels also applies to fixed methods of DNA analysis. In these latter methods, the DNA is tagged differentially, and then either scanned or imaged. In a fluorescence-based system, for instance, the above example of resolving three sites within the optical resolution of the system would provide a representative image as such is shown in FIG. 8.

In this one example, three simultaneous images are captures from the spectrally separated signals arising from the sample. The images are then overlayed and the spatial positions determined with sub-optical resolution accuracy. The center of each of the emissions from the sequence-specific tags and the center-to-center distance spacing is determined from the captured image. It is expected that there will be a population of molecules in the image that represent molecules having different combinations of fluorescent tags attached to the target sites. In the imaging pictures above, it is expected that there would be combinations of RRR, GGG, RGR, GRG, RRG, and so on where R=red and G=green. A large enough number of molecules should be sampled in order to obtain a sufficient number of molecules with alternating patterns of differentially tagged tags. The alternating pattern allows deconvolution of the number of tags within the optical resolution limit.

EQUIVALENTS

The foregoing written specification is to be considered to be sufficient to enable one skilled in the art to practice the invention. The examples disclosed herein are not to be construed as limiting of the invention as they are intended merely as illustrative of particular embodiments of the invention as enabled herein. Therefore, systems that are functionally equivalent to those described herein are within the spirit and scope of the claims appended hereto. Indeed, various modifications of the invention in addition to those shown and described herein will become apparent to those skilled in the art from the foregoing description and fall within the scope of the appended claims.

All references, patents and patent publications that are recited in this application are incorporated in their entirety herein by reference.

We claim:

1. A method for analyzing a polymer comprising:
providing the polymer having first and second unit specific markers, the first unit specific marker including a first label and the second unit specific marker including a second label, wherein the first and second unit specific markers are spaced apart on the polymer by a separation distance;
providing a detection zone adapted to detect emission signals, the detection zone characterized by a zone distance;
moving the polymer through the detection zone at a velocity;
detecting signals emitted from the label of the first unit specific marker before and after a first timing event as the first unit specific marker passes through the detection zone, to define a first emission signal;
calculating a proportion of the first emission signal that corresponds to a distance of the detection zone traversed by the label of the first unit specific marker at the first timing event;
detecting signals emitted from the label of the second unit specific marker before and after a second timing event as the second unit specific marker passes through the detection zone, to define a second emission signal;
calculating a proportion of the second emission signal that corresponds to a distance of the detection zone traversed by the label of the second unit specific marker at the second timing event;
determining the separation distance at a precision greater than the zone distance by comparing the proportion of the first emission signal and the proportion of the second emission signal; and
outputting an indication of the separation distance to a user.

2. The method of claim 1, wherein calculating the proportion of the first emission signal that corresponds to the distance of the detection zone that has been traversed by the label of the first unit specific marker at the first timing event comprises dividing the signal emitted from the label of the first unit specific marker before the first timing event by the first emission signal.

3. The method of claim 2, wherein calculating the proportion of the second emission signal that corresponds to the distance of the detection zone that has been traversed by the label of the second unit specific marker at the second timing event comprises dividing the signal emitted from the label of the second unit specific marker before the second timing event by the second emission signal.

4. The method of claim 1, wherein calculating the proportion of the first emission signal that corresponds to the distance of the detection zone that has been traversed by the label of the first unit specific marker at the first timing event comprises dividing the signal emitted from the label of the first unit specific marker after the first timing event by the first emission signal.

5. The method of claim 4, wherein calculating the proportion of the second emission signal that corresponds to the distance of the detection zone that has been traversed by the label of the second unit specific marker at the second timing event comprises dividing the signal emitted from the label of the second unit specific marker after the second timing event by the second emission signal.

6. The method of claim 1, wherein the first label and the second label are distinct types of labels.

7. The method of claim 6, wherein the first and second timing events are a single timing event for calculating the proportion of the first emission signal and calculating the proportion of the second emission signal.

8. The method of claim 7, wherein determining the separation distance comprises multiplying the proportion of the first signal and the proportion of the second signal by the zone distance to define a first distance and a second distance, respectively; and
then subtracting the second distance from the first distance to define the separation distance.

9. The method of claim 7, wherein determining the separation distance comprises
subtracting the proportion of the second signal from the proportion of the first signal to define a separation factor; and
then multiplying the separation factor by the zone distance to define the separation distance.

10. The method of claim 6, wherein the first and second timing events comprise two distinct timing events, the first timing event for calculating the proportion of the first emission signal and the second timing event that occurs one reset time immediately after the first timing event, the second timing event for calculating the proportion of the second emission signal.

11. The method of claim 10, further comprising:
calculating a reset distance by multiplying the velocity by the reset time;
wherein determining the separation distance comprises
multiplying the proportion of the first signal and the proportion of the second signal by the zone distance to define a first distance and a second distance, respectively;
then subtracting the second distance from the first distance; and
then adding the reset distance to the first distance to define the separation distance.

12. The method of claim 10, further comprising:
calculating a reset distance by multiplying the velocity by the reset time;
wherein determining the separation distance comprises
subtracting the proportion of the second signal from the proportion of the first signal to define a separation factor;
then multiplying the separation factor by the zone distance; and
then adding the reset distance to define the separation distance.

13. The method of claim 1, wherein the first and second timing events comprise two distinct timing events, the first timing event for calculating the proportion of the first emission signal and the second timing event that occurs later and is separated by one or more timing events within a series of timing events, the second timing event for calculating the proportion of the second emission signal.

14. The method of claim 13, further comprising:
calculating a reset distance by multiplying the velocity by the reset time;
wherein determining the separation distance comprises
multiplying the proportion of the first emission signal and the proportion of the second emission signal by the zone distance to define a first distance and a second distance, respectively; and
further wherein the second distance is subtracted from the first distance and a number of reset distances equivalent to the number of timing events, are added to the first distance to define the separation distance.

15. The method of claim 13, further comprising:
calculating a reset distance by multiplying the velocity by the reset time;
wherein determining the separation distance comprises
subtracting the proportion of the second emission signal from the proportion of the first emission signal; and
further wherein the separation factor is multiplied by the zone distance and a number of reset distances, equivalent to the number of timing events, are added to define the separation distance.

16. The method of claim 14, wherein the first label and the second label comprise similar types of labels.

17. The method of claim 14, wherein the first label and the second label are distinct types of labels.

18. The method of claim 15, wherein the first label and the second label comprise similar types of labels.

19. The method of claim 15, wherein the first label and the second label are distinct types of labels.

20. The method of claim 19, wherein the first unit specific marker is different from the second unit specific marker.

21. The method of claim 18, wherein the first unit specific marker is identical to the second unit specific marker.

22. The method of claim 21, wherein the polymer is labeled with a third unit specific marker comprising a third label.

23. The method of claim 1, wherein the first and second unit specific markers are nucleic acid molecules.

24. The method of claim 1, wherein the first and second unit specific markers are peptide nucleic acid molecules or locked nucleic acid molecules.

25. The method of claim 1, wherein the first and second unit specific markers have an identical nucleotide sequence.

26. The method of claim 1, wherein the first and second unit specific markers are less than 12 bases in length.

27. The method of claim 1, wherein the first and second unit specific markers are at least 4 bases in length.

28. The method of claim 1, wherein the first label and second label are selected from the group consisting of an electron spin resonance molecule, a fluorescent molecule, a chemiluminescent molecule, a radioisotope, an enzyme substrate, an enzyme, a biotin molecule, an avidin molecule, an electrical charge transferring molecule, a semiconductor nanocrystal, a semiconductor nanoparticle, a colloid gold nanocrystal, a ligand, a microbead, a magnetic bead, a paramagnetic molecule, a quantum dot, a chromogenic substrate, an affinity molecule, a protein, a peptide, a nucleic acid, a carbohydrate, a hapten, an antigen, an antibody, an antibody fragment, and a lipid.

29. The method of claim 1, wherein the signals are detected using a detection system selected from the group consisting of an electron spin resonance (ESR) detection system, a charge coupled device (CCD) detection system, a fluorescent detection system, an electrical detection system, an electromagnetic detection system, a photographic film detection system, a chemiluminescent detection system, an enzyme detection system, an atomic force microscopy (AFM) detection system, a scanning tunneling microscopy (STM) detection system, an optical detection system, a nuclear magnetic resonance (NMR) detection system, a near field detection system, and a total internal reflection (TIR) detection system.

30. The method of claim 1, wherein the polymer is a nucleic acid molecule.

31. The method of claim 1, wherein the polymer is genomic DNA or RNA.

32. The method of claim 1, wherein the polymer comprises a backbone that includes a label.

33. The method of claim 10, wherein the reset time is between 0.01 and 1000 milliseconds.

34. The method of claim 1, wherein the detection zone is circular and the zone distance is a diameter of the detection zone.

35. A method comprising:
moving through a detection zone a polymer bound to a first labeled unit specific marker and a second labeled unit specific marker, wherein the first and second unit specific markers are spaced apart by a separation distance, detecting signals that define a first emission signal and are emitted from the first labeled unit specific marker, before and after a first timing event, as the first labeled unit specific marker pass through the detection zone, detecting signals that define a second emission signal and are emitted from the second labeled unit specific marker, before and after a second timing event, as the second labeled unit specific marker passes through the detection zone, calculating a proportion of the first emission signal that corresponds to a distance of the detection zone traversed by the first labeled unit specific marker at the first timing event, calculating a proportion of the second emission signal that corresponds to a distance of the detection zone traversed by the second labeled unit specific marker at the second timing event, determining the separation distance at a precision greater than the zone distance by comparing the proportion of the first emission signal and the proportion of the second emission signal; and outputting an indication of the separation distance to a user.

* * * * *